US012037384B2

(12) United States Patent
Crowe, Jr.

(10) Patent No.: US 12,037,384 B2
(45) Date of Patent: Jul. 16, 2024

(54) HUMAN MONOCLONAL ANTIBODIES AGAINST YELLOW FEVER VIRUS AND USES THEREFOR

(71) Applicant: VANDERBILT UNIVERSITY, Nashville, TN (US)

(72) Inventor: James E. Crowe, Jr., Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 17/816,114

(22) Filed: Jul. 29, 2022

(65) Prior Publication Data

US 2023/0072640 A1    Mar. 9, 2023

Related U.S. Application Data

(60) Provisional application No. 63/230,163, filed on Aug. 6, 2021.

(51) Int. Cl.
| | |
|---|---|
| *C07K 16/10* | (2006.01) |
| *A61P 31/14* | (2006.01) |
| *G01N 33/569* | (2006.01) |
| *A61K 39/00* | (2006.01) |

(52) U.S. Cl.
CPC .......... *C07K 16/1081* (2013.01); *A61P 31/14* (2018.01); *G01N 33/56983* (2013.01); *A61K 2039/505* (2013.01); *C07K 2317/24* (2013.01); *C07K 2317/565* (2013.01); *C07K 2317/76* (2013.01); *C07K 2317/92* (2013.01); *G01N 2469/10* (2013.01)

(58) Field of Classification Search
CPC ............ C07K 16/1081; C07K 2317/24; C07K 2317/565; C07K 2317/76; C07K 2317/92; C07K 2317/21; C07K 2317/34; A61P 31/14; G01N 33/56983; G01N 2469/10; G01N 2333/185; A61K 2039/505
See application file for complete search history.

(56) References Cited

PUBLICATIONS

Brandriss, M W et al. "Lethal 17D yellow fever encephalitis in mice. I. Passive protection by monoclonal antibodies to the envelope proteins of 17D yellow fever and dengue 2 viruses," *The Journal of general virology* vol. 67 ( Pt 2) (1986): 229-34.

Cammack, N, and E A Gould. "Topographical analysis of epitope relationships on the envelope glycoprotein of yellow fever 17D vaccine and the wild type Asibi parent virus." *Virology* vol. 150,2 (1986): 333-41.

Haslwanter, Denise et al. "A novel mechanism of antibody-mediated enhancement of flavivirus infection." *PLoS pathogens* vol. 13,9 e1006643. Sep. 15, 2017.

Julander, Justin G et al. "Humanized monoclonal antibody 2C9-cIgG has enhanced efficacy for yellow fever prophylaxis and therapy in an immunocompetent animal model." *Antiviral research* vol. 103 (2014): 32-8.

Lu, Xishan et al. "Double Lock of a Human Neutralizing and Protective Monoclonal Antibody Targeting the Yellow Fever Virus Envelope." *Cell reports* vol. 26,2 (2019): 438-446.e5.

Pierson, Theodore C, and Margaret Kielian. "Flaviviruses: braking the entering." *Current opinion in virology* vol. 3,1 (2013): 3-12.

Putnak, J R, and J J Schlesinger. "Protection of mice against yellow fever virus encephalitis by immunization with a vaccinia virus recombinant encoding the yellow fever virus non-structural proteins, NS1, NS2a and NS2b." *The Journal of general virology* vol. 71 ( Pt 8) (1990): 1697-702.

Ryman, K D et al. "Yellow fever virus envelope protein bas two discrete type-specific neutralizing epitopes." *The Journal of general virology* vol. 78 ( Pt 6) (1997): 1353-6.

Schlesinger, J J et al. "Monoclonal antibodies distinguish between wild and vaccine strains of yellow fever virus by neutralization, hemagglutination inhibition, and immune precipitation of the virus envelope protein." *Virology* vol. 125,1 (1983): 8-17.

Schlesinger, J J et al. "Protection against 17D yellow fever encephalitis in mice by passive transfer of monoclonal antibodies to the nonstructural glycoprotein gp48 and by active immunization with gp48." *Journal of immunology* (Baltimore, Md. : 1950) vol. 135,4 (1985): 2805-9.

Schlesinger, J J et al. "The Fc portion of antibody to yellow fever virus NS1 is a determinant of protection against YF encephalitis in mice." *Virology* vol. 192,1 (1993): 132-41.

Thibodeaux, Brett A et al. "A humanized IgG but not IgM antibody is effective in prophylaxis and therapy of yellow fever infection in an AG129/17D-204 peripheral challenge mouse model." *Antiviral research* vol. 94,1 (2012): 1-8.

Wec, Anna Z et al. "Longitudinal dynamics of the human B cell response to the yellow fever 17D vaccine," *Proceedings of the National Academy of Sciences of the United States of America* vol. 117,12 (2020): 6675-6685.

*Primary Examiner* — Nelson B Moseley, II
(74) *Attorney, Agent, or Firm* — Parker Highlander PLLC

(57) ABSTRACT

The present disclosure is directed to antibodies binding to and neutralizing Yellow Fever Virus and methods for use thereof.

27 Claims, 8 Drawing Sheets
Specification includes a Sequence Listing.

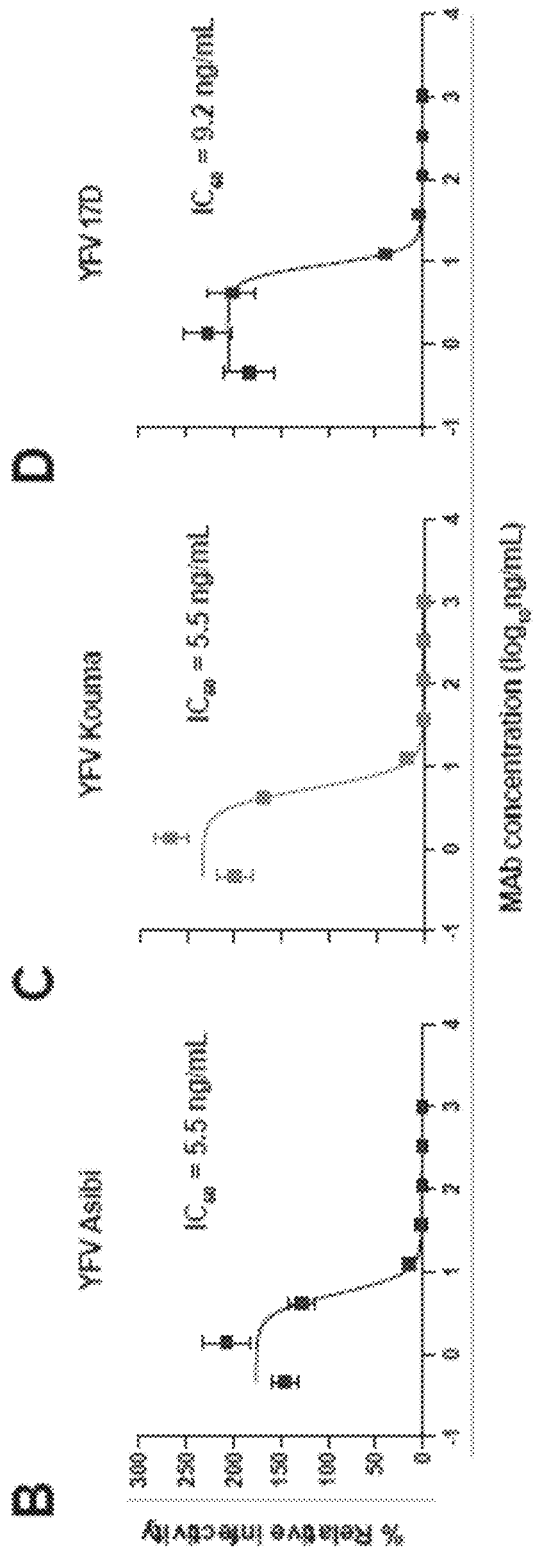
FIGS. 2B-D

FIGS. 3A-C

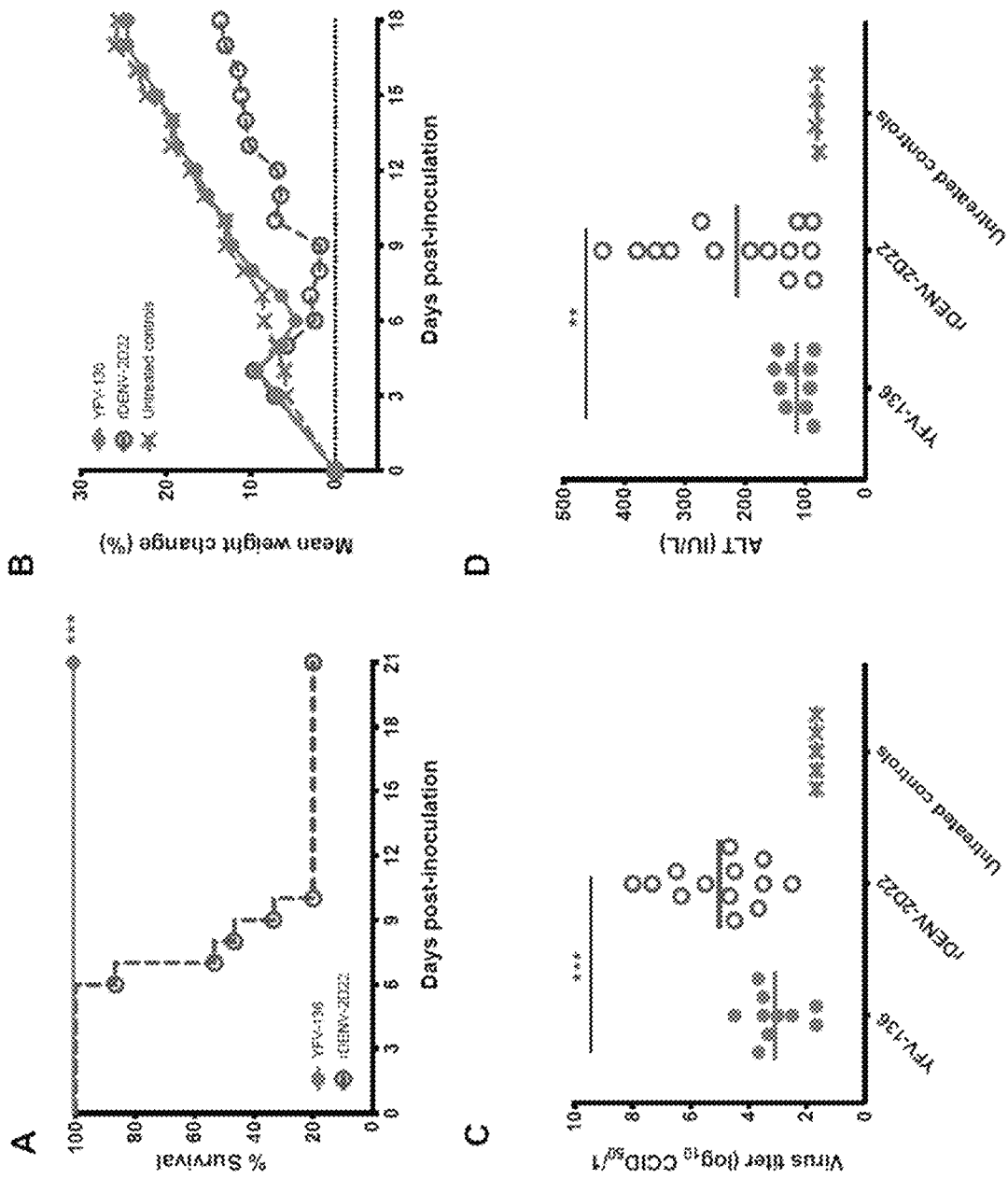
FIGS. 4A-D

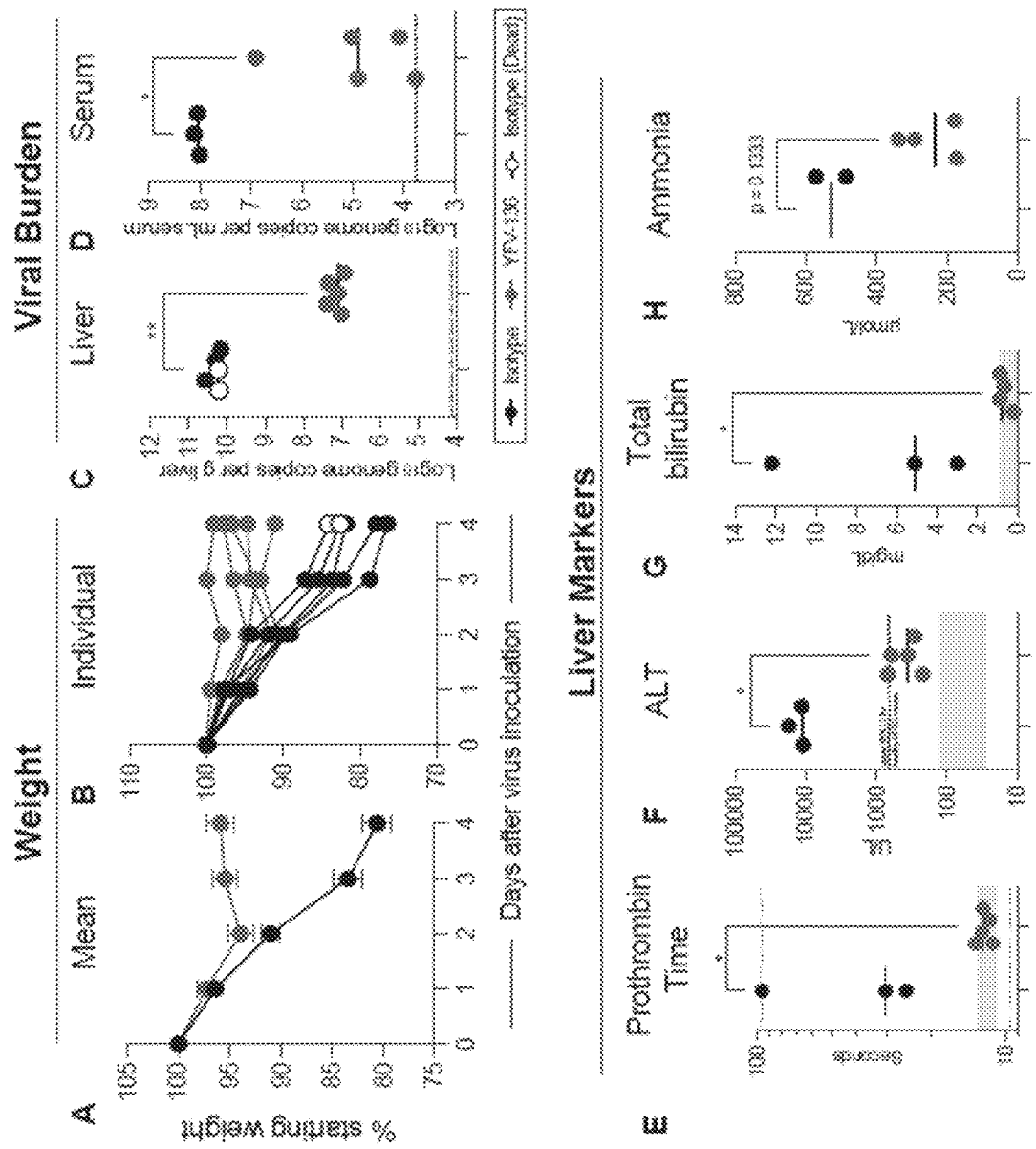
FIGS. 5A-H

B

| Start | End | Amino Acid Sequence |
|---|---|---|
| 31 | 41 | VTVMAPDKPSL |
| 62 | 82 | NAVLTHVKINDKCPSTGEAHL |
| 63 | 82 | AVLTHVKINDKCPSTGEAHL |
| 83 | 107 | AEENEGDNACKRTYSDRGWGNGCGL |
| 108 | 116 | FGKGSIVAC |
| 128 | 137 | FEVDQTKIQY |
| 144 | 152 | HVGAKQENW |
| 213 | 224 | LTLPWQSGSGGV |
| 242 | 254 | IRVLALGNQEGSL |
| 242 | 258 | IRVLALGNQEGSLKTAL |
| 290 | 301 | LTLKGTSYKICT |
| 350 | 360 | VTVNPIASTND |

FIG. 6B

HUMAN MONOCLONAL ANTIBODIES AGAINST YELLOW FEVER VIRUS AND USES THEREFOR

PRIORITY CLAIM

This application claims benefit of priority to U.S. Provisional Application Ser. No. 63/230,163, filed Aug. 6, 2021, the entire contents of which are hereby incorporated by reference.

INCORPORATION BY REFERENCE

This application contains a Sequence Listing XML, which has been submitted electronically and is hereby incorporated by reference in its entirety. Said XML Sequence Listing, created on Jul. 29, 2022, is named VBLTP0318_.xml and is 29,433 bytes in size.

BACKGROUND

1. Field of the Disclosure

The present disclosure relates generally to the fields of medicine, infectious disease, and immunology. More particular, the disclosure relates to human antibodies binding to Yellow Fever Virus E protein.

2. Background

Yellow fever virus (YFV), the prototype and namesake member of the family Flaviviridae, is a historically important human pathogen. Yellow fever disease has been described in the New World since the 1600s, and YFV was first identified in 1927 (Bauer and Hudson, 1928). The virus has caused numerous epidemics of human disease throughout the world. According to the World Health Organization, 47 countries in Africa and Central and South America currently have regions endemic for yellow fever, and the burden of yellow fever disease during 2019 was as high as 109,000 severe cases and 51,000 deaths (Gaythorpe et al., 2021). Approximately thirty percent of infected individuals develop severe disease that includes hemorrhagic complications and multiorgan failure, half of which succumb to the infection (Monath and Vasconcelos, 2015). Non-human primates serve as the primary reservoir for YFV, with mosquitoes in the *Haemogogus* and *Sabethes* genera serving as the vectors responsible for maintenance the reservoir and spillover into humans in what is referred to as the "sylvatic cycle." Once within the human population, YFV is spread primarily by a different vector, the anthropophilic *Aedes aegyptii* mosquito, in an "urban cycle" (Douam and Ploss, 2018). With infections becoming more frequent in urban centers like Sao Paolo and Rio de Janeiro, there is concern that more severe YFV epidemics may occur in the future (Cunha et al., 2020).

YFV is an enveloped virus with a positive-sense, single-stranded RNA genome. The YFV genome is translated as a single polyprotein, which is post-translationally cleaved by a combination of host and viral proteins into 3 structural (pr/M, E, C) and 7 non-structural (NS1, NS2a, NS2b, NS3, NS4a, NS4b, NS5) proteins (Chambers et al., 1990). The envelope (E) protein is the primary surface-exposed protein on mature particles and is the principal target of the protective humoral immune system (Daffis et al., 2005). The E protein is comprised of three domains (domain I (DI), DII, and DIII). DII contains a number of immunodominant epitopes, including the fusion loop (FL), which mediates fusion of viral and host membranes in the late endosome. Domain III on E contains the putative cellular attachment domain (Pierson and Kielan, 2013). While several attachment factors have been postulated, specific entry receptors for YFV have not yet been identified. The virus enters host cells by receptor-mediated endocytosis, where the low pH of late endosomes triggers conformational changes in the E protein. These changes expose the FL, which inserts into the endosomal membrane, allowing penetration of the RNA genome into the host cytoplasm for translation and replication. Although E protein is the primary target of neutralizing antibodies (Ryman et al., 1997; Brandriss et al., 1986; Cammack and Gould, 1986; Schlesinger et al., 1983, non-structural 1 (NS1) proteins also can elicit protective antibodies (Schlesinger et al., 1985; Schlesinger et al., 1993; Putnak and Schlesinger, 1990). Conversely, prM antibodies may confer the risk of antibody-dependent enhancement of infection by otherwise poorly infectious immature virions (Smith et al., 2016; Dejnirattisai et al., 2010; Rodenhius-Zybert et al., 2010).

The YFV vaccine, based on a strain known as 17D, was created by serial passage and attenuation in the 1930s by Max Theiler and is considered one of the most successful vaccines to date ever created. However, production of 17D has changed little since its inception, resulting in a system of manufacturing and distribution that have been unable to keep pace with demand: —400 million people in endemic areas still require vaccination to achieve the herd-immunity threshold required to prevent urban spread of YFV (Shearer et al., 2017). Fractional dosing has been explored in outbreak settings when vaccine supply is insufficient, but there is a lack of consensus on the effectiveness of this strategy (Casey et al., 2019; Wilder-Smith et al., 2019). YFV vaccine shortages stem principally from the limitations inherent in the legacy methods of vaccine strain propagation still being used. When outbreaks do occur in the setting of vaccine insufficiency, specific licensed antiviral treatments targeting YFV are not available.

Recently, potent neutralizing monoclonal antibodies (mAbs) against a number of viral targets have shown efficacy as potential treatments of highly pathogenic agents, including other flaviviruses. Several such antibodies targeting YFV have been described. A mAb designated A5 was identified using phage display technology and showed efficacy in an immunodeficient YFV-17D challenge model (Lu et al., 2019). A humanized monoclonal antibody designated 2C9 showed benefit in hamsters against Jimenez strain (Julander et al., 2014) and in AG129 mice against YFV 17D-204 challenge (Thibodeaux et al., 2012), supporting the proof of principle for antibodies as a medical countermeasure for YFV. Fully human mAbs with native heavy and light chain pairing, however, are preferred for use in human therapy.

SUMMARY

Thus, in accordance with the present disclosure, 1. A method of detecting a Yellow Fever Virus (YFV) infection in a subject comprising (a) contacting a sample from said subject with an antibody or antibody fragment having clone-paired heavy and light chain CDR sequences from Tables 3 and 4, respectively; and (b) detecting YFV in said sample by binding of said antibody or antibody fragment to a YFV antigen in said sample. The sample may be a body fluid, or may be blood, sputum, tears, saliva, mucous or serum, semen, cervical or vaginal secretions, amniotic fluid, placental tissues, urine, exudate, transudate, tissue scrapings or feces. Detection may comprise ELISA, RIA, lateral flow assay or Western blot. The method may further comprise performing steps (a) and (b) a second time and determining a change in YFV antigen levels as compared to the first assay.

The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')2 fragment, or Fv fragment.

In another embodiment, there is provided a method of treating a subject infected with Yellow Fever Virus (YFV), or reducing the likelihood of infection of a subject at risk of contracting YFV, comprising delivering to said subject an antibody or antibody fragment having clone-paired heavy and light chain CDR sequences from Tables 3 and 4, respectively. The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')2 fragment, or Fv fragment. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, LALA-PG, N297, GASD/ALIE, DHS, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody.

The antibody or antibody fragment may be administered prior to infection or after infection. The subject may be a pregnant female, a sexually active female, or a female undergoing fertility treatments. Delivering may comprise antibody or antibody fragment administration, or genetic delivery with an RNA or DNA sequence or vector encoding the antibody or antibody fragment.

In yet another embodiment, there is provided a monoclonal antibody, wherein the antibody or antibody fragment is characterized by clone-paired heavy and light chain CDR sequences from Tables 3 and 4, respectively. The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')2 fragment, or Fv fragment. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, LALA-PG, N297, GASD/ALIE, DHS, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The antibody or antibody fragment may further comprise a cell penetrating peptide and/or is an intrabody.

In still yet another embodiment, there is provided a hybridoma or engineered cell encoding an antibody or antibody fragment wherein the antibody or antibody fragment is characterized by clone-paired heavy and light chain CDR sequences from Tables 3 and 4, respectively. The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')2 fragment, or Fv fragment. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, LALA-PG, N297, GASD/ALIE, DHS, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The antibody or antibody fragment may further comprise a cell penetrating peptide and/or is an intrabody.

In a further embodiment, there is provided a vaccine formulation comprising one or more antibodies or antibody fragments characterized by clone-paired heavy and light chain CDR sequences from Tables 3 and 4, respectively. The at least antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The at least antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The at least antibody fragment may be a recombinant scFv (single chain fragment variable) antibody, Fab fragment, F(ab')2 fragment, or Fv fragment. The at least antibody may be an IgG, or a recombinant IgG antibody or antibody fragment comprising an Fc portion mutated to alter (eliminate or enhance) FcR interactions, to increase half-life and/or increase therapeutic efficacy, such as a LALA, LALA-PG, N297, GASD/ALIE, DHS, YTE or LS mutation or glycan modified to alter (eliminate or enhance) FcR interactions such as enzymatic or chemical addition or removal of glycans or expression in a cell line engineered with a defined glycosylating pattern. The at least antibody may be a chimeric antibody or a bispecific antibody. The antibody or antibody fragment may further comprise a cell penetrating peptide and/or is an intrabody.

In an even further embodiment, there is provided a vaccine formulation comprising one or more expression vectors encoding a first antibody or antibody fragment as defined herein. The expression vector(s) may be Sindbis virus or VEE vector(s). The formulation may be formulated for delivery by needle injection, jet injection, or electroporation. The formulation may further comprise one or more expression vectors encoding for a second antibody or antibody fragment, such as a distinct antibody or antibody fragment of claims 26-34.

An additional embodiment is a method of protecting the health of a placenta and/or fetus of a pregnant a subject infected with or at risk of infection with Yellow Fever Virus comprising delivering to said subject an antibody or antibody fragment having clone-paired heavy and light chain CDR sequences from Tables 3 and 4, respectively. The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')2 fragment, or Fv fragment. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, LALA-PG, N297, GASD/ALIE, DHS, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The antibody or antibody fragment may further comprise a cell penetrating peptide and/or is an intrabody.

The antibody or antibody fragment maybe administered prior to infection or after infection. The subject may be a pregnant female, a sexually active female, or a female undergoing fertility treatments. Delivering may comprise antibody or antibody fragment administration, or genetic delivery with an RNA or DNA sequence or vector encoding the antibody or antibody fragment. The antibody or antibody fragment may increase the size of the placenta as compared to an untreated control. The antibody or antibody fragment may reduce viral load and/or pathology of the fetus as compared to an untreated control.

A further embodiment is a method of determining the antigenic integrity, correct conformation and/or correct sequence of a Yellow Fever Virus antigen comprising (a) contacting a sample comprising said antigen with a first antibody or antibody fragment having clone-paired heavy and light chain CDR sequences from Tables 3 and 4, respectively; and (b) determining antigenic integrity, correct conformation and/or correct sequence of said antigen by detectable binding of said first antibody or antibody fragment to said antigen. The sample may comprise recombinantly produced antigen or a vaccine formulation or vaccine production batch. Detection may comprise ELISA, RIA, western blot, a biosensor using surface plasmon resonance or biolayer interferometry, or flow cytometric staining.

The first antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The first antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')2 fragment, or Fv fragment. The method may further comprise performing steps (a) and (b) a second time to determine the antigenic stability of the antigen over time.

The method may further comprise (c) contacting a sample comprising said antigen with a second antibody or antibody fragment having clone-paired heavy and light chain CDR sequences from Tables 3 and 4, respectively; and (d) determining antigenic integrity of said antigen by detectable binding of said second antibody or antibody fragment to said antigen. The second antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The second antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The second antibody fragment may be a recombinant scFv (single chain fragment variable) antibody, Fab fragment, F(ab')2 fragment, or Fv fragment. The method may further comprise performing steps (c) and (d) a second time to determine the antigenic stability of the antigen over time.

Also provided is a human monoclonal antibody or antibody fragment, or hybridoma or engineered cell producing the same, wherein said antibody binds to Yellow Fever Virus (YFV) (a) binds to H67 in domain II of YFV E protein; (b) neutralizes multiple trains of YFV; and/or (c) interacts with both E protomers within the dimeric, membrane bound structure of YFV-E.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A-B. ELISA binding and FRNT neutralization by human mAbs targeting YFV E protein. (FIG. 1A) Half maximal effective concentrations (EC50) of antibody binding to YFV E as determined by ELISA. Values were interpolated using a non-linear regression model in Prism software. Data from a single experiment are shown, representative of three independent experiments. (FIG. 1B). Focus reduction neutralization test (FRNT) to assess neutralization of YFV-17D by YFV-121 and YFV-136. Neutralization values were fit to a non-linear regression model. Data from a single experiment are shown, representing at least two independent experiments.

FIGS. 2A-D. Competition binding and neutralization by human mAbs targeting YFV E protein. (FIG. 2A) Octet biolayer interferometry competition binding of human mAbs against YFV E. Antibodies listed top to bottom were associated to immobilized YFV E protein, with antibodies shown left to right tested for their ability to bind in the presence of the first antibody. Binding is expressed as a percentage of residual binding, with black boxed indicating compete competition, gray boxed partial competition, and white boxes no competition. Antibodies were clustered based on their competition profiles and labeled A-F. (FIGS. 2B-D) Neutralization of diverse YFV strains assessed by a focus reduction neutralization test (FRNT). Values were fit to a non-linear regression model using Prism software. Three independent experiments were performed in technical triplicate, with data from a single representative experiment shown.

FIGS. 3A-C. Investigation of antigenic site and mechanism of action of YFV-136. (FIG. 3A) Cell impedance measurements during a first round of YFV-17D escape mutant virus selection. Each box represents the cell impedance within a single well of a 96-well plate as a function of time. The * symbol indicates wells that exhibit a drop in cell impedance at late time points, suggesting viral escape in the presence of 5 µg/mL YFV-136. A single well marked with # was used as a control for cell culture adaptation. * and # wells were propagated once more in culture on the device, and finally in 6-well culture dishes in the presence of 10 µg/mL YFV-136 (or no antibody for #) to allow for viral outgrowth. Viral RNA was isolated and prM and E genes amplified by RT-PCR using primers flanking the prM and E genes. These same primers, and two other primers targeting internal prM and/or E sequences, were used to sequence virus isolated from * and # by Sanger sequencing. These sequences were aligned in Geneious software to identify point mutations. (FIG. 3B) Escape mutant identified in panel A mapped onto the crystal structure of YFV E (PDB 6IW5). (FIG. 3C) Focus reduction neutralization test of YFV-136 at pre- or post-attachment of virus to host cells. Neutralization values were assessed using a non-linear regression model in Prism software. Two independent experiments were performed in technical triplicate, with data from a single representative experiment shown.

FIGS. 4A-D. Syrian golden hamster challenge studies to assess YFV-136 therapeutic efficacy. (FIG. 4A) Kaplan-Meier survival curves of animals treated with 50 mg/kg YFV-136 or 20 mg/kg isotype control 3 days post-inoculation with 200×CCID$_{50}$ hamster-adapted YFV Jimenez strain. Statistical analysis was performed using a Wilcoxon Log-Rank test. (FIG. 4B) Weight maintenance of animals treated with YFV-136, isotype control, or uninoculated animals throughout the course of the study. (FIG. 4C) Serum virus titers (50% cell culture infectious doses [CCID$_{50}$]) were assessed 6 days after virus inoculation. A one-way ANOVA with Dunnett's multiple comparisons was used to assess statistical significance. (FIG. 4D) Serum alanine aminotransferase (ALT) levels at 6 days after inoculation was assessed as a proxy for liver damage. A one-way ANOVA with Dunnett's multiple comparisons was used to assess statistical significance.

FIGS. 5A-H. hFRG challenge studies to assess YFV-136 therapeutic efficacy. FRG mice engrafted with human hepatocytes (hFRG) were inoculated with $2 \times 10^5$ focus forming units (FFU) of wt YFV-Dakar. Eight hr later, mice were administered a single 10 mg/kg dose of YFV-136 (n=5, grey points) or isotype control (n=5, black points) 8 hrs post-inoculation. Note, two of the control mAb-treated YFV-infected mice succumbed to infection at 4 dpi (denoted by open circles), and thus some serum-based measurements were not available. (FIGS. 5A-B). Weight loss showing mean values (FIG. 5A) and individual animal profiles (FIG. 5B). FIGS. 5C-D. Viral burden measures at 4 dpi in the liver (FIG. 5C) and serum (FIG. 5D) as measured by RT-qPCR. FIGS. 5E-H. Serum biomarkers of hepatic injury at 4 dpi. Samples were tested for prothrombin time (E), alanine aminotransferase (ALT, FIG. 5F), total bilirubin (FIG. 5G), and ammonia (FIG. 5H) levels. (FIGS. 5C-H). Mann-Whitney test (*, $p<0.05$; **, $p<0.01$). Bars denote median values. Dashed lines in FIG. 5C and FIG. 5D indicate the (lower and/or upper) limit of detection of the assay. Grey boxes indicate the reference range for each parameter in mice; for ALT a dashed line is shown to denote the upper limit of "normal" for healthy hFRG mice at baseline.

FIGS. 6A-B. Epitope mapping for Fab YFV-136 by hydrogen/deuterium exchange (HDX) mass spectrometry (MS). (FIG. 6A) Representative kinetic plots for the 12 different peptides showing the effects of Fab binding by HDX. Black or green lines are for YFV E protein in the absence or presence of the mAb YFV-136, respectively. At the top of each panel are the residue numbers and charge states of the peptide. (FIG. 6B) Sequences and positions of each peptide.

DESCRIPTION OF ILLUSTRATIVE EMBODIMENTS

Figure 6A:
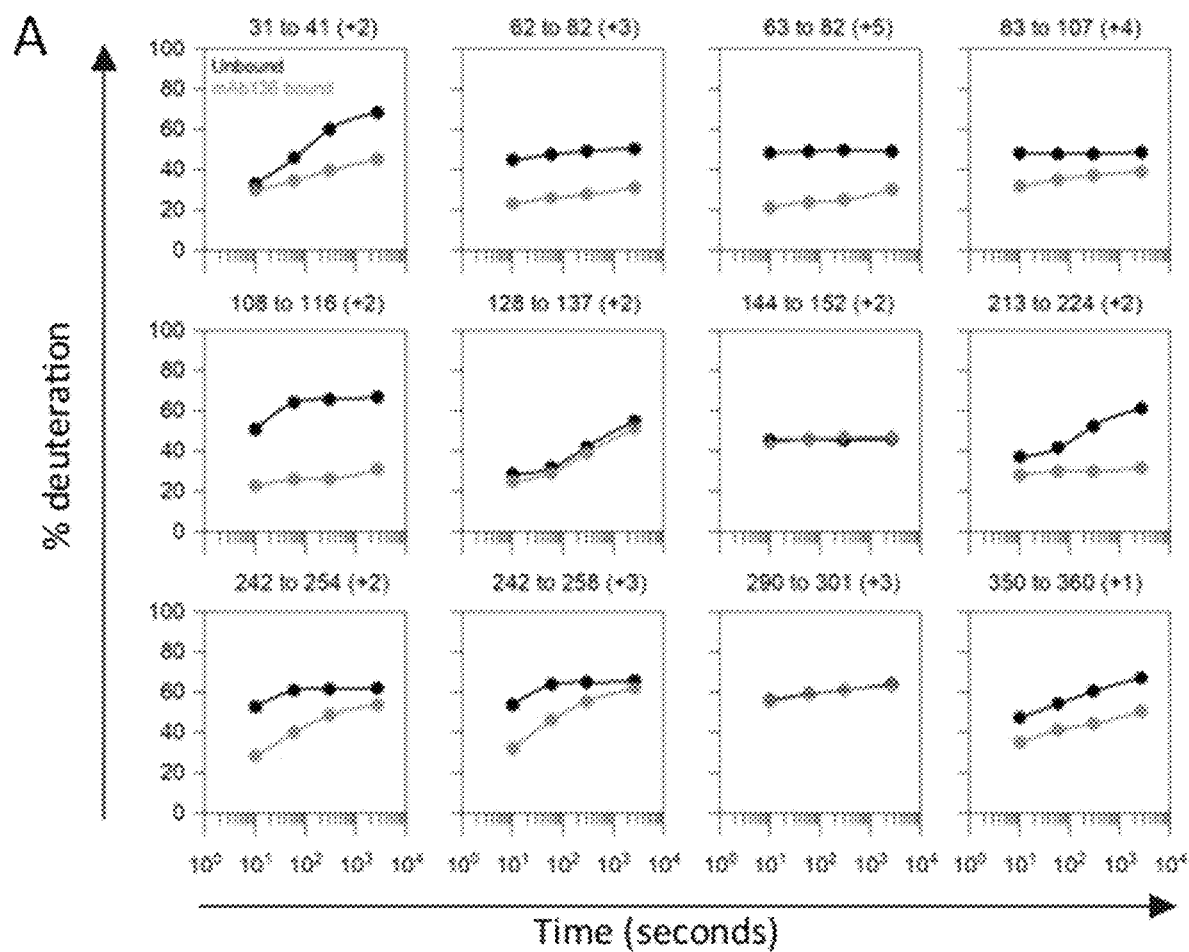

As discussed above, YFV remains a significant health challenge around the world, even today. In an attempt to generate improved therapies for YFV infection, the inventor isolated a panel of fully human mAbs targeting E protein to identify candidate therapeutic antibodies. Competition-binding studies mapped these antibodies to several antigenic sites, one of which elicits antibodies that neutralize YFV. In vitro studies of one of the most potent neutralizing mAbs, designated YFV-136, revealed that this antibody exerts its neutralizing activity at least partially at a post-attachment step via binding to DII on YFV E protein. Neutralization escape virus selection revealed a critical residue on DII that, when substituted from histidine to tyrosine, allows for viral escape from YFV-136 neutralization. Passive transfer of YFV-136 mAb protected against lethal YFV challenge in a therapeutic challenge setting in two small animal models, Syrian golden hamsters and immunocompromised mice engrafted with human hepatocytes. These studies identify a potently neutralizing mAb targeting YFV and pave the way for further development of human mAb YFV-136 as a possible candidate therapeutic agent.

These and other aspects of the disclosure are described in detail below.

I. YELLOW FEVER AND YELLOW FEVER VIRUS (YFV)

Yellow fever is one of a group of hemorrhagic fevers. Typically short duration, yellow fever can be severe and is highly fatal in such cases with death occurring in up to half of those who get severe disease. The disease is caused by yellow fever virus (YFV) and is spread by the bite of an infected mosquito. It infects only humans, other primates, and several types of mosquitoes. In cities, it is spread primarily by *Aedes aegypti*, a type of mosquito found throughout the tropics and subtropics. The virus is an RNA virus of the genus Flavivirus. The disease may be difficult to tell apart from other illnesses, especially in the early stages. To confirm a suspected case, blood-sample testing with polymerase chain reaction is required.

In 2013, yellow fever resulted in about 127,000 severe infections and 45,000 deaths worldwide, with nearly 90 percent of these occurring in Africa. Nearly a billion people live in an area of the world where the disease is common. It is common in tropical areas of the continents of South America and Africa, but not in Asia. Since the 1980s, the number of cases of yellow fever has been increasing This is believed to be due to fewer people being immune, more people living in cities, people moving frequently, and changing climate increasing the habitat for mosquitoes.

The disease originated in Africa and spread to South America in the 17th century with the Spanish and Portuguese importation of enslaved Africans from sub-Saharan Africa. Since the 17th century, several major outbreaks of the disease have occurred in the Americas, Africa, and Europe. In the 18th and 19th centuries, yellow fever was considered one of the most dangerous infectious diseases; numerous epidemics swept through major cities of the US and in other parts of the world. In 1927, YFV was the first human virus to be isolated.

Yellow fever begins after an incubation period of three to six days. Most cases cause only a mild infection with fever, headache, chills, back pain, fatigue, loss of appetite, muscle pain, nausea, and vomiting. In these cases, the infection lasts only three to six days. But in 15% of cases, people enter a second, toxic phase of the disease characterized by recurring fever, this time accompanied by jaundice due to liver damage, as well as abdominal pain. Bleeding in the mouth, nose, the eyes, and the gastrointestinal tract cause vomit containing blood, hence the Spanish name for yellow fever, vómito negro ("black vomit"). There may also be kidney failure, hiccups, and delirium. Among those who develop jaundice, the fatality rate is 20 to 50%, while the overall fatality rate is about 3 to 7.5%. Severe cases may have a mortality greater than 50%. Surviving the infection provides lifelong immunity, and normally results in no permanent organ damage.

YFV is an enveloped RNA virus 40-50 nm in width, the type species and namesake of the family Flaviviridae. The positive-sense, single-stranded RNA is around 10.862 nucleotides long and has a single open reading frame encoding a polyprotein. Host proteases cut this polyprotein into three structural (C, prM, E) and seven nonstructural proteins (NS1, NS2A, NS2B, NS3, NS4A, NS4B, NS5); the enumeration corresponds to the arrangement of the protein coding genes in the genome. Minimal YFV 3'UTR region is required for stalling of the host 5'-3' exonuclease XRN1. The UTR contains PKS3 pseudoknot structure, which serves as a molecular signal to stall the exonuclease and is the only viral requirement for subgenomic flavivirus RNA (sfRNA) production. The sfRNAs are a result of incomplete degradation of the viral genome by the exonuclease and are important for viral pathogenicity.

The viruses infect, amongst others, monocytes, macrophages, Schwann cells, and dendritic cells. They attach to the cell surfaces via specific receptors and are taken up by an endosomal vesicle. Inside the endosome, the decreased pH induces the fusion of the endosomal membrane with the virus envelope. The capsid enters the cytosol, decays, and releases the genome. Receptor binding, as well as membrane fusion, are catalyzed by the protein E, which changes its conformation at low pH, causing a rearrangement of the 90 homodimers to 60 homotrimers.

After entering the host cell, the viral genome is replicated in the rough endoplasmic reticulum (ER) and in the so-called vesicle packets. At first, an immature form of the virus particle is produced inside the ER, whose M-protein is not yet cleaved to its mature form, so is denoted as precursor M (prM) and forms a complex with protein E. The immature particles are processed in the Golgi apparatus by the host protein furin, which cleaves prM to M. This releases E protein from the complex, which can now take its place in the mature, infectious virion.

As with other Flavivirus infections, no cure is known for yellow fever. Hospitalization is advisable and intensive care may be necessary because of rapid deterioration in some cases. Certain acute treatment methods lack efficacy: passive immunization after the emergence of symptoms is probably without effect; ribavirin and other antiviral drugs, as well as treatment with interferons, are ineffective in yellow fever patients. Symptomatic treatment includes rehydration and pain relief with drugs such as paracetamol (acetaminophen). Acetylsalicylic acid (aspirin). However, aspirin and other non-steroidal anti-inflammatory drugs (NSAIDs) are often avoided because of an increased risk of gastrointestinal bleeding due to their anticoagulant effects.

Yellow fever virus is mainly transmitted through the bite of the yellow fever mosquito Aedes aegypti, but other mostly Aedes mosquitoes such as the tiger mosquito (Aedes albopictus) can also serve as a vector for this virus. Like other arboviruses, which are transmitted by mosquitoes, yellow fever virus is taken up by a female mosquito when it ingests the blood of an infected human or another primate. Viruses reach the stomach of the mosquito, and if the virus concentration is high enough, the virions can infect epithelial cells and replicate there. From there, they reach the haemocoel (the blood system of mosquitoes) and from there the salivary glands. When the mosquito next sucks blood, it injects its saliva into the wound, and the virus reaches the bloodstream of the bitten person. Transovarial and transstadial transmission of yellow fever virus within A. aegypti, that is, the transmission from a female mosquito to her eggs and then larvae, are indicated. This infection of vectors without a previous blood meal seems to play a role in single, sudden breakouts of the disease.

Three epidemiologically different infectious cycles occur in which the virus is transmitted from mosquitoes to humans or other primates. In the "urban cycle", only the yellow fever mosquito A. aegypti is involved. It is well adapted to urban areas, and can also transmit other diseases, including Zika fever, dengue fever, and chikungunya. The urban cycle is responsible for the major outbreaks of yellow fever that occur in Africa. Except for an outbreak in Bolivia in 1999, this urban cycle no longer exists in South America.

Besides the urban cycle, both in Africa and South America, a sylvatic cycle (forest or jungle cycle) is present, where Aedes africanus (in Africa) or mosquitoes of the genus Haemagogus and Sabethes (in South America) serve as vectors. In the jungle, the mosquitoes infect mainly nonhuman primates; the disease is mostly asymptomatic in African primates. In South America, the sylvatic cycle is currently the only way humans can become infected, which explains the low incidence of yellow fever cases on the continent. People who become infected in the jungle can carry the virus to urban areas, where A. aegypti acts as a vector. Because of this sylvatic cycle, yellow fever cannot be eradicated except by eradicating the mosquitoes that serve as vectors.

In Africa, a third infectious cycle known as "savannah cycle" or intermediate cycle, occurs between the jungle and urban cycles. Different mosquitoes of the genus Aedes are involved. In recent years, this has been the most common form of transmission of yellow fever in Africa.

Yellow fever is most frequently a clinical diagnosis, based on symptomatology and travel history. Mild cases of the disease can only be confirmed virologically. Since mild cases of yellow fever can also contribute significantly to regional outbreaks, every suspected case of yellow fever (involving symptoms of fever, pain, nausea, and vomiting 6-10 days after leaving the affected area) is treated seriously. If yellow fever is suspected, the virus cannot be confirmed until 6-10 days following the illness. A direct confirmation can be obtained by reverse transcription polymerase chain reaction, where the genome of the virus is amplified. Another direct approach is the isolation of the virus and its growth in cell culture using blood plasma; this can take 1-4 weeks.

Serologically, an enzyme-linked immunosorbent assay during the acute phase of the disease using specific IgM against yellow fever or an increase in specific IgG titer (compared to an earlier sample) can confirm yellow fever. Together with clinical symptoms, the detection of IgM or a four-fold increase in IgG titer is considered sufficient indication for yellow fever. As these tests can cross-react with other flaviviruses, such as dengue virus, these indirect methods cannot conclusively prove yellow fever infection.

Liver biopsy can verify inflammation and necrosis of hepatocytes and detect viral antigens. Because of the bleeding tendency of yellow fever patients, a biopsy is only advisable post mortem to confirm the cause of death.

In a differential diagnosis, infections with yellow fever must be distinguished from other feverish illnesses such as malaria. Other viral hemorrhagic fevers, such as Ebola virus, Lassa virus, Marburg virus, and Junin virus, must be excluded as the cause.

Personal prevention of yellow fever includes vaccination and avoidance of mosquito bites in areas where yellow fever is endemic. Institutional measures for prevention of yellow fever include vaccination programs and measures to control mosquitoes. Programs for distribution of mosquito nets for use in homes produce reductions in cases of both malaria and yellow fever. Use of EPA-registered insect repellent is recommended when outdoors. Exposure for even a short time is enough for a potential mosquito bite. Long-sleeved clothing, long pants, and socks are useful for prevention. The application of larvicides to water-storage containers can help eliminate potential mosquito breeding sites. EPA-registered insecticide spray decreases the transmission of yellow fever.

Use of insect repellent when outdoors such as those containing DEET, picaridin, ethyl butylacetylaminopropionate (IR3535), or oil of lemon Eucalyptus on exposed skin, wearing proper clothing to reduce mosquito bites are recommended in high risk areas as well as vaccination for those traveling to such affected areas. Non-native people tend to develop more severe illness when infected. Protection begins by the 10th day after vaccine administration in 95% of people, and had been reported to last for at least 10 years. The World Health Organization (WHO) now states that a single dose of vaccine is sufficient to confer lifelong immunity against yellow fever disease.

An attenuated live vaccine stem 17D was developed in 1937 by Max Theiler. The WHO recommends routine vaccination for people living in affected areas between the 9th and 12th month after birth. Up to one in four people experience fever, aches, and local soreness and redness at the site of injection. In rare cases (less than one in 200,000 to 300,000), the vaccination can cause yellow fever vaccine-associated viscerotropic disease, which is fatal in 60% of cases. It is probably due to the genetic morphology of the immune system. Another possible side effect is an infection of the nervous system, which occurs in one in 200,000 to 300,000 cases, causing yellow fever vaccine-associated neurotropic disease, which can lead to meningoencephalitis and is fatal in less than 5% of cases.

Demand for yellow fever vaccine has continued to increase due to the growing number of countries implementing yellow fever vaccination as part of their routine immunization programmes. Recent upsurges in yellow fever outbreaks in Angola (2015), the Democratic Republic of Congo (2016), Uganda (2016), and more recently in Nigeria and Brazil in 2017 have further increased demand, while straining global vaccine supply. Therefore, to vaccinate susceptible populations in preventive mass immunization campaigns during outbreaks, fractional dosing of the vaccine is being considered as a dose-sparing strategy to maximize limited vaccine supplies. Fractional dose yellow fever vaccination refers to administration of a reduced volume of vaccine dose, which has been reconstituted as per manufacturer recommendations. The first practical use of fractional dose yellow fever vaccination was in response to a large yellow fever outbreak in the Democratic Republic of the Congo in mid-2016.

In March 2017, the WHO launched a vaccination campaign in Brazil with 3.5 million doses from an emergency stockpile. In March 2017 the WHO recommended vaccination for travellers to certain parts of Brazil. In March 2018, Brazil shifted its policy and announced it planned to vaccinate all 77.5 million currently unvaccinated citizens by April 2019.

II. Monoclonal Antibodies and Production Thereof

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In particular embodiments, the antibody is purified: (1) to greater than 95% by weight of antibody as determined by the Lowry method, and most particularly more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

The basic four-chain antibody unit is a heterotetrameric glycoprotein composed of two identical light (L) chains and two identical heavy (H) chains. An IgM antibody consists of 5 basic heterotetramer units along with an additional polypeptide called J chain, and therefore contain 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable region ($V_H$) followed by three constant domains ($C_H$) for each of the alpha and gamma chains and four $C_H$ domains for mu and isotypes. Each L chain has at the N-terminus, a variable region ($V_L$) followed by a constant domain ($C_L$) at its other end. The $V_L$ is aligned with the $V_H$ and the $C_L$ is aligned with the first constant domain of the heavy chain ($C_H$O. Particular amino acid residues are believed to form an interface between the light chain and heavy chain variable regions. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The L chain from any vertebrate species can be assigned to one of two clearly distinct types, called kappa and lambda based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha, delta, epsilon, gamma and mu, respectively. They gamma and alpha classes are further divided into subclasses on the basis of relatively minor differences in $C_H$ sequence and function, humans express the following subclasses: IgG1, IgG2, IgG3, IgG4, IgA1, and IgA2.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable regions. Instead, the V regions consist of relatively invariant stretches called framework regions (FRs) of 15-30 amino acids separated by shorter regions of extreme variability called "hypervariable regions" that are each 9-12 amino acids long. The variable regions of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC), antibody-dependent cellular phagocytosis (ADCP), antibody-dependent neutrophil phagocytosis (ADNP), and antibody-dependent complement deposition (ADCD).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system; Lefranc, M. P. et al. Nucl. Acids Res. 27:209-212 (1999), Ruiz, M. et al. Nucl. Acids Res. 28:219-221 (2000)). Optionally the antibody has symmetrical insertions at one or more of the following points 28, 36 (L1), 63, 74-75 (L2) and 123

(L3) in the $V_L$, and 28, 36 (H1), 63, 74-75 (H2) and 123 (H3) in the $V_{sub}H$ when numbered in accordance with AHo; Honneger, A. and Plunkthun, A. J. Mol. Biol. 309:657-670 (2001)).

By "germline nucleic acid residue" is meant the nucleic acid residue that naturally occurs in a germline gene encoding a constant or variable region. "Germline gene" is the DNA found in a germ cell (i.e., a cell destined to become an egg or in the sperm). A "germline mutation" refers to a heritable change in a particular DNA that has occurred in a germ cell or the zygote at the single-cell stage, and when transmitted to offspring, such a mutation is incorporated in every cell of the body. A germline mutation is in contrast to a somatic mutation which is acquired in a single body cell. In some cases, nucleotides in a germline DNA sequence encoding for a variable region are mutated (i.e., a somatic mutation) and replaced with a different nucleotide.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present disclosure may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567) after single cell sorting of an antigen specific B cell, an antigen specific plasmablast responding to an infection or immunization, or capture of linked heavy and light chains from single cells in a bulk sorted antigen specific collection. The "monoclonal antibodies" may also be isolated from phage antibody libraries using the techniques described in Clackson et al., Nature, 352:624-628 (1991) and Marks et al., J. Mol. Biol., 222: 581-597 (1991), for example.

A. General Methods

It will be understood that monoclonal antibodies binding to YFV will have several applications. These include the production of diagnostic kits for use in detecting and diagnosing YFV infection, as well as for treating the same. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host or identification of subjects who are immune due to prior natural infection or vaccination with a licensed or experimental vaccine. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants in animals include complete Freund's adjuvant (a non-specific stimulator of the immune response containing killed *Mycobacterium tuberculosis*), incomplete Freund's adjuvants and aluminum hydroxide adjuvant and in humans include alum, CpG, MFP59 and combinations of immunostimulatory molecules ("Adjuvant Systems", such as AS01 or AS03). Additional experimental forms of inoculation to induce YFV-specific B cells is possible, including nanoparticle vaccines, or gene-encoded antigens delivered as DNA or RNA genes in a physical delivery system (such as lipid nanoparticle or on a gold biolistic bead), and delivered with needle, gene gun, transcutaneous electroporation device. The antigen gene also can be carried as encoded by a replication competent or defective viral vector such as adenovirus, adeno-associated virus, poxvirus, herpesvirus, or alphavirus replicon, or alternatively a virus like particle.

In the case of human antibodies against natural pathogens, a suitable approach is to identify subjects that have been exposed to the pathogens, such as those who have been diagnosed as having contracted the disease, or those who have been vaccinated to generate protective immunity against the pathogen or to test the safety or efficacy of an experimental vaccine. Circulating anti-pathogen antibodies can be detected, and antibody encoding or producing B cells from the antibody-positive subject may then be obtained.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens, lymph nodes, tonsils or adenoids, bone marrow aspirates or biopsies, tissue biopsies from mucosal organs like lung or GI tract, or from circulating blood. The antibody-producing B lymphocytes from the immunized animal or immune human are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984). HMMA2.5 cells or MFP-2 cells are particularly useful examples of such cells.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. In some cases, transformation of human B cells with Epstein Barr virus (EBV) as an initial step increases the size of the B cells, enhancing fusion with the relatively large-sized myeloma cells. Transformation efficiency by EBV is enhanced by using CpG and a Chk2 inhibitor drug in the transforming medium. Alternatively, human B cells can be activated by co-culture with transfected cell lines expressing CD40 Ligand (CD154) in medium containing additional soluble factors, such as IL-21 and human B cell Activating Factor (BAFF), a Type II member of the TNF superfamily. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986) and there are processes for better efficiency (Yu et al., 2008). Fusion procedures usually produce viable hybrids at low frequencies, about $1\times10^{-6}$ to $1\times10^{-8}$, but with optimized procedures one can achieve fusion efficiencies close to 1 in 200 (Yu et al., 2008). However, relatively low efficiency of fusion does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture medium. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the medium is supplemented with hypoxanthine and thymidine as a source of nucleotides (HAT medium). Where azaserine is used, the medium is supplemented with hypoxanthine. Ouabain is added if the B cell source is an EBV-transformed human B cell line, in order to eliminate EBV-transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain may also be used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonal antibodies. Single B cells labelled with the antigen of interest can be sorted physically using paramagnetic bead selection or flow cytometric sorting, then RNA can be isolated from the single cells and antibody genes amplified by RT-PCR. Alternatively, antigen-specific bulk sorted populations of cells can be segregated into microvesicles and the matched heavy and light chain variable genes recovered from single cells using physical linkage of heavy and light chain amplicons, or common barcoding of heavy and light chain genes from a vesicle. Matched heavy and light chain genes form single cells also can be obtained from populations of antigen specific B cells by treating cells with cell-penetrating nanoparticles bearing RT-PCR primers and barcodes for marking transcripts with one barcode per cell. The antibody variable genes also can be isolated by RNA extraction of a hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

Antibodies according to the present disclosure may be defined, in the first instance, by their binding specificity. Those of skill in the art, by assessing the binding specificity/affinity of a given antibody using techniques well known to those of skill in the art, can determine whether such antibodies fall within the scope of the instant claims. For example, the epitope to which a given antibody bind may consist of a single contiguous sequence of 3 or more (e.g., 3, 4, 5, 6, 7, 8, 9, 10, 11, 12, 13, 14, 15, 16, 17, 18, 19, 20) amino acids located within the antigen molecule (e.g., a linear epitope in a domain). Alternatively, the epitope may consist of a plurality of non-contiguous amino acids (or amino acid sequences) located within the antigen molecule (e.g., a conformational epitope).

Various techniques known to persons of ordinary skill in the art can be used to determine whether an antibody "interacts with one or more amino acids" within a polypeptide or protein, Exemplary techniques include, for example, routine cross-blocking assays, such as that described in Antibodies, Harlow and Lane (Cold Spring Harbor Press, Cold Spring Harbor, N.Y.), Cross-blocking can be measured in various binding assays such as EISA, biolayer interferometry, or surface plasmon resonance. Other methods include alanine scanning mutational analysis, peptide blot analysis (Reineke (2004) Methods Mol. Biol. 248: 443-63), peptide cleavage analysis, high-resolution electron microscopy techniques using single particle reconstruction, cryoEM, or tomography, crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antibody interacts is hydrogen/deuterium exchange detected by mass spectrometry. In general term, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267: 252-259; Engen and Smith (2001) Anal. Chem. 73: 256A-265A. When the antibody neutralizes YFV, antibody escape mutant variant organisms can be isolated by propagating YFV in vitro or in animal models in the presence of high concentrations of the antibody. Sequence analysis of a YFV gene encoding the antigen targeted by the antibody reveals the mutation(s) conferring antibody escape, indicating residues in the epitope or that affect the structure of the epitope allosterically.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics, MAP may be used to sort the antibodies of the disclosure into groups of antibodies binding different epitopes.

The present disclosure includes antibodies that may bind to the same epitope, or a portion of the epitope. Likewise, the present disclosure also includes antibodies that compete for binding to a target or a fragment thereof with any of the specific exemplary antibodies described herein, One can easily determine whether an antibody binds to the same epitope as, or competes for binding with, a reference antibody by using routine methods known in the art. For example, to determine if a test antibody binds to the same epitope as a reference, the reference antibody is allowed to bind to target under saturating conditions. Next, the ability of a test antibody to bind to the target molecule is assessed. If the test antibody is able to bind to the target molecule following saturation binding with the reference antibody, it can be concluded that the test antibody binds to a different epitope than the reference antibody. On the other hand, if the test antibody is not able to bind to the target molecule following saturation binding with the reference antibody, then the test antibody may bind to the same epitope as the epitope bound by the reference antibody.

To determine if an antibody competes for binding with a reference anti-YFV antibody, the above-described binding methodology is performed in two orientations: In a first orientation, the reference antibody is allowed to bind to the YFV antigen under saturating conditions followed by assessment of binding of the test antibody to the YFV antigen. In a second orientation, the test antibody is allowed to bind to the YFV antigen molecule under saturating conditions followed by assessment of binding of the reference antibody to the YFV antigen. If, in both orientations, only the first (saturating) antibody is capable of binding to the YFV antigen, then it is concluded that the test antibody and the reference antibody compete for binding to the YFV. As win be appreciated by a person of ordinary skill in the art, an antibody that competes for binding with a reference antibody may not necessarily bind to the identical epitope as the reference antibody but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art. Structural studies with EM or crystallography also can demonstrate whether or not two antibodies that compete for binding recognize the same epitope.

In another aspect, there are provided monoclonal antibodies having clone-paired CDRs from the heavy and light chains as illustrated in Tables 3 and 4, respectively. Such antibodies may be produced by the clones discussed below in the Examples section using methods described herein.

In another aspect, the antibodies may be defined by their variable sequence, which include additional "framework" regions. These are provided in Tables 1 and 2 that encode or represent full variable regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (f) the amino acids may vary from those set out above by permitting conservative substitutions (discussed below). Each of the foregoing applies to the nucleic acid sequences set forth as Table 1 and the amino acid sequences of Table 2.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogeny pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor 11:105; Santou, N. Nes, M. (1987) Mol. Biol. Evol. 4:406-425; Sneath, P. H. A. and Sokal, R. R. (1973) Numerical Taxonomy—the Principles and Practice of Numerical Taxonomy, Freeman Press, San Francisco, Calif.; Wilbur, W. J. and Lipman, D. J. (1983) Proc. Natl. Acad., Sci. USA 80:726-730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One particular example of algorithms that are suitable for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403-410, respectively. BLAST and BLAST 2.0 can be used, for example, with the parameters described herein, to determine percent sequence identity for the polynucleotides and polypeptides of the disclosure. Software for performing BLAST analyses is publicly available through the National Center for Biotechnology Information. The rearranged nature of an antibody sequence and the variable length of each gene requires multiple rounds of BLAST searches for a single antibody sequence. Also, manual assembly of different genes is difficult and error-prone. The sequence analysis tool IgBLAST (world-wide-web at ncbi.nlm.nih.gov/igblast/) identifies matches to the germline V, D and J genes, details at rearrangement junctions, the delineation of Ig V domain framework regions and complementarity determining regions. IgBLAST can analyze nucleotide or protein sequences and can process sequences in batches and allows searches against the germline gene databases and other sequence databases simultaneously to minimize the chance of missing possibly the best matching germline V gene.

In one illustrative example, cumulative scores can be calculated using, for nucleotide sequences, the parameters M (reward score for a pair of matching residues; always >0) and N (penalty score for mismatching residues; always <0).

Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) Proc. Natl. Acad. Sci. USA 89:10915) alignments, (B) of 50, expectation (E) of 10, M=5, N=−4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

Yet another way of defining an antibody is as a "derivative" of any of the below-described antibodies and their antigen-binding fragments. The term "derivative" refers to an antibody or antigen-binding fragment thereof that immunospecifically binds to an antigen but which comprises, one, two, three, four, five or more amino acid substitutions, additions, deletions or modifications relative to a "parental" (or wild-type) molecule. Such amino acid substitutions or additions may introduce naturally occurring (i.e., DNA-encoded) or non-naturally occurring amino acid residues. The term "derivative" encompasses, for example, as variants having altered CH1, hinge, CH2, CH3 or CH4 regions, so as to form, for example, antibodies, etc., having variant Fc regions that exhibit enhanced or impaired effector or binding characteristics. The term "derivative" additionally encompasses non-amino acid modifications, for example, amino acids that may be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment, the altered carbohydrate modifications enhance antibody mediated effector function relative to the antibody lacking the carbohydrate modification. Carbohydrate modifications that lead to altered antibody mediated effector function are well known in the art (for example, see Shields, R. L. et al. (2002), J. Biol. Chem. 277(30): 26733-26740; Davies J. et al. (2001), Biotechnology & Bioengineering 74(4): 288-294). Methods of altering carbohydrate contents are known to those skilled in the art, see, e.g., Wallick, S. C. et al. (1988), J. Exp. Med. 168(3): 1099-1109; Tao, M. H. et al. (1989), J. Immunol. 143(8): 2595-2601; Routledge, E. G. et al. (1995), Transplantation 60(8):847-53; Elliott, S. et al. (2003), Nature Biotechnol. 21:414-21; Shields, R. L. et al. (2002), J. Biol. Chem. 277(30): 26733-26740).

A derivative antibody or antibody fragment can be generated with an engineered sequence or glycosylation state to confer preferred levels of activity in antibody dependent cellular cytotoxicity (ADCC), antibody-dependent cellular phagocytosis (ADCP), antibody-dependent neutrophil phagocytosis (ADNP), or antibody-dependent complement deposition (ADCD) functions as measured by bead-based or cell-based assays or in vivo studies in animal models.

A derivative antibody or antibody fragment may be modified by chemical modifications using techniques known to those of skill in the art, including, but not limited to, specific chemical cleavage, acetylation, formulation, metabolic synthesis of tunicamycin, etc. In one embodiment, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody.

C. Engineering of Antibody Sequences

In various embodiments, one may choose to engineer sequences of the identified antibodies for a variety of reasons, such as improved expression, improved cross-reactivity or diminished off-target binding. Modified antibodies may be made by any technique known to those of skill in the art, including expression through standard molecular biological techniques, or the chemical synthesis of polypeptides. Methods for recombinant expression are addressed elsewhere in this document. The following is a general discussion of relevant goals techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full-length IgG antibodies can be generated by subcloning heavy and light chain Fv DNAs from the cloning vector into an IgG plasmid vector, transfected into 293 (e.g., Freestyle) cells or CHO cells, and antibodies can be collected and purified from the 293 or CHO cell supernatant. Other appropriate host cells systems include bacteria, such as E. coli, insect cells (S2, Sf9, Sf29, High Five), plant cells (e.g., tobacco, with or without engineering for human-like glycans), algae, or in a variety of non-human transgenic contexts, such as mice, rats, goats or cows.

Expression of nucleic acids encoding antibodies, both for the purpose of subsequent antibody purification, and for immunization of a host, is also contemplated. Antibody coding sequences can be RNA, such as native RNA or modified RNA. Modified RNA contemplates certain chemical modifications that confer increased stability and low immunogenicity to mRNAs, thereby facilitating expression of therapeutically important proteins. For instance, N1-methyl-pseudouridine (N1mψ) outperforms several other nucleoside modifications and their combinations in terms of translation capacity. In addition to turning off the immune/eIF2a phosphorylation-dependent inhibition of translation, incorporated N1mψ nucleotides dramatically alter the dynamics of the translation process by increasing ribosome pausing and density on the mRNA. Increased ribosome loading of modified mRNAs renders them more permissive for initiation by favoring either ribosome recycling on the same mRNA or de novo ribosome recruitment. Such modifications could be used to enhance antibody expression in vivo following inoculation with RNA. The RNA, whether native or modified, may be delivered as naked RNA or in a delivery vehicle, such as a lipid nanoparticle.

Alternatively, DNA encoding the antibody may be employed for the same purposes. The DNA is included in an expression cassette comprising a promoter active in the host cell for which it is designed. The expression cassette is advantageously included in a replicable vector, such as a conventional plasmid or minivector. Vectors include viral vectors, such as poxviruses, adenoviruses, herpesviruses, adeno-associated viruses, and lentiviruses are contemplated. Replicons encoding antibody genes such as alphavirus replicons based on VEE virus or Sindbis virus are also contemplated. Delivery of such vectors can be performed by needle through intramuscular, subcutaneous, or intradermal routes, or by transcutaneous electroporation when in vivo expression is desired.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), F(ab')2) that are produced, for example, by the proteolytic cleavage of the mAbs, or single-chain immunoglobulins producible, for example, via recombinant means. F(ab') antibody derivatives are monovalent, while F(ab')2 antibody derivatives are bivalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to IgG$_1$ can increase antibody dependent cell cytotoxicity, switching to class A can improve tissue distribution, and switching to class M can improve valency.

Alternatively or additionally, it may be useful to combine amino acid modifications with one or more further amino acid modifications that alter C1q binding and/or the complement dependent cytotoxicity (CDC) function of the Fc region of an IL-23p19 binding molecule. The binding polypeptide of particular interest may be one that binds to C1q and displays complement dependent cytotoxicity. Polypeptides with pre-existing C1q binding activity, optionally further having the ability to mediate CDC may be modified such that one or both of these activities are enhanced. Amino acid modifications that alter C1q and/or modify its complement dependent cytotoxicity function are described, for example, in WO/0042072, which is hereby incorporated by reference.

One can design an Fc region of an antibody with altered effector function, e.g., by modifying C1q binding and/or FcγR binding and thereby changing CDC activity and/or ADCC activity. "Effector functions" are responsible for activating or diminishing a biological activity (e.g., in a subject). Examples of effector functions include, but are not limited to: C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions may require the Fc region to be combined with a binding domain (e.g., an antibody variable domain) and can be assessed using various assays (e.g., Fc binding assays, ADCC assays, CDC assays, etc.).

For example, one can generate a variant Fc region of an antibody with improved C1q binding and improved FcγRIII binding (e.g., having both improved ADCC activity and improved CDC activity). Alternatively, if it is desired that effector function be reduced or ablated, a variant Fc region can be engineered with reduced CDC activity and/or reduced ADCC activity. In other embodiments, only one of these activities may be increased, and, optionally, also the other activity reduced (e.g., to generate an Fc region variant with improved ADCC activity, but reduced CDC activity and vice versa).

FcRn binding. Fc mutations can also be introduced and engineered to alter their interaction with the neonatal Fc receptor (FcRn) and improve their pharmacokinetic properties. A collection of human Fc variants with improved binding to the FcRn have been described (Shields et al., (2001). High resolution mapping of the binding site on human IgG1 for FcγRI, FcγRII, FcγRIII, and FcRn and design of IgG1 variants with improved binding to the FcγR, (J. Biol. Chem. 276:6591-6604). A number of methods are known that can result in increased half-life (Kuo and Aveson, (2011)), including amino acid modifications may be generated through techniques including alanine scanning mutagenesis, random mutagenesis and screening to assess the binding to the neonatal Fc receptor (FcRn) and/or the in vivo behavior. Computational strategies followed by mutagenesis may also be used to select one of amino acid mutations to mutate.

The present disclosure therefore provides a variant of an antigen binding protein with optimized binding to FcRn. In a particular embodiment, the said variant of an antigen binding protein comprises at least one amino acid modification in the Fc region of said antigen binding protein, wherein said modification is selected from the group consisting of 226, 227, 228, 230, 231, 233, 234, 239, 241, 243, 246, 250, 252, 256, 259, 264, 265, 267, 269, 270, 276, 284, 285, 288, 289, 290, 291, 292, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 384, 385, 386, 387, 389, 390, 392, 393, 394, 395, 396, 397, 398, 399, 400, 401403, 404, 408, 411, 412, 414, 415, 416, 418, 419, 420, 421, 422, 424, 426, 428, 433, 434, 438, 439, 440, 443, 444, 445, 446 and 447 of the Fc region as compared to said parent polypeptide, wherein the numbering of the amino acids in the Fc region is that of the EU index in Kabat. In a further aspect of the disclosure the modifications are M252Y/S254T/T256E.

Additionally, various publications describe methods for obtaining physiologically active molecules whose half-lives are modified, see for example Kontermann (2009) either by introducing an FcRn-binding polypeptide into the molecules or by fusing the molecules with antibodies whose FcRn-binding affinities are preserved but affinities for other Fc receptors have been greatly reduced or fusing with FcRn binding domains of antibodies.

Derivatized antibodies may be used to alter the half-lives (e.g., serum half-lives) of parental antibodies in a mammal, particularly a human. Such alterations may result in a half-life of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies of the present disclosure or fragments thereof in a mammal, preferably a human, results in a higher serum titer of said antibodies or antibody fragments in the mammal, and thus reduces the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor.

Beltramello et al. (2010) previously reported the modification of neutralizing mAbs, due to their tendency to enhance dengue virus infection, by generating in which leucine residues at positions 1.3 and 1.2 of CH2 domain (according to the IMGT unique numbering for C-domain) were substituted with alanine residues. This modification, also known as "LALA" mutation, abolishes antibody binding to FcγRI, FcγRII and FcγRIIIa, as described by Hessell et al. (2007). The variant and unmodified recombinant mAbs were compared for their capacity to neutralize and enhance infection by the four dengue virus serotypes. LALA variants retained the same neutralizing activity as unmodified mAb but were completely devoid of enhancing activity. Lo et al. 2017 reported an alternate set of Fc mutations L234A, L235A, with an added P329G mutation (designated LALA-PG) that eliminates complement binding and fixation as well as Fc-γ-dependent, antibody-dependent, cell-mediated cytotoxicity in both murine IgG2.a and human IgG1.LALA or LALA-PG (Lo et al., 2017) mutations of this nature are therefore contemplated in the context of the presently disclosed antibodies.

Altered Glycosylation. A particular embodiment of the present disclosure is an isolated monoclonal antibody, or antigen binding fragment thereof, containing a substantially homogeneous glycan without sialic acid, galactose, or fucose. The monoclonal antibody comprises a heavy chain variable region and a light chain variable region, both of which may be attached to heavy chain or light chain constant regions respectively. The aforementioned substantially homogeneous glycan may be covalently attached to the heavy chain constant region.

Another embodiment of the present disclosure comprises a mAb with a novel Fc glycosylation pattern. The isolated monoclonal antibody, or antigen binding fragment thereof, is present in a substantially homogenous composition represented by the GNGN or G1/G2 glycoform. Fc glycosylation plays a significant role in anti-viral and anti-cancer properties of therapeutic mAbs. The disclosure is in line with a recent study that shows increased anti-lentivirus cell-mediated viral inhibition of a fucose free anti-HIV mAb in vitro. This embodiment of the present disclosure with homogenous glycans lacking a core fucose, showed increased protection against specific viruses by a factor greater than two-fold. Elimination of core fucose dramatically improves the ADCC activity of mAbs mediated by natural killer (NK)

cells but appears to have the opposite effect on the ADCC activity of polymorphonuclear cells (PMNs).

The isolated monoclonal antibody, or antigen binding fragment thereof, comprising a substantially homogenous composition represented by the GNGN or G1/G2 glycoform exhibits increased binding affinity for Fc gamma RI and Fc gamma RIII compared to the same antibody without the substantially homogeneous GNGN glycoform and with G0, G1F, G2F, GNF, GNGNF or GNGNFX containing glycoforms. In one embodiment of the present disclosure, the antibody dissociates from Fc gamma RI with a Kd of $1 \times 10^{-8}$ M or less and from Fc gamma RIII with a Kd of $1 \times 10^{-7}$ M or less.

Glycosylation of an Fc region is typically either N-linked or O-linked. N-linked refers to the attachment of the carbohydrate moiety to the side chain of an asparagine residue. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used. The recognition sequences for enzymatic attachment of the carbohydrate moiety to the asparagine side chain peptide sequences are asparagine-X-serine and asparagine-X-threonine, where X is any amino acid except proline. Thus, the presence of either of these peptide sequences in a polypeptide creates a potential glycosylation site.

The glycosylation pattern may be altered, for example, by deleting one or more glycosylation site(s) found in the polypeptide, and/or adding one or more glycosylation site(s) that are not present in the polypeptide. Addition of glycosylation sites to the Fc region of an antibody is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites). Additionally, a change of Asn 297 to Ala can remove one of the glycosylation sites.

In certain embodiments, the antibody is expressed in cells that express beta (1,4)-N-acetylglucosaminyltransferase III (GnT III), such that GnT III adds GlcNAc to the IL-23p19 antibody. Methods for producing antibodies in such a fashion are provided in WO/9954342, WO/03011878, patent publication 20030003097A1, and Umana et al., Nature Biotechnology, 17:176-180, February 1999. Cell lines can be altered to enhance or reduce or eliminate certain post-translational modifications, such as glycosylation, using genome editing technology such as Clustered Regularly Interspaced Short Palindromic Repeats (CRISPR). For example, CRISPR technology can be used to eliminate genes encoding glycosylating enzymes in 293 or CHO cells used to express recombinant monoclonal antibodies.

Elimination of monoclonal antibody protein sequence liabilities. It is possible to engineer the antibody variable gene sequences obtained from human B cells to enhance their manufacturability and safety. Potential protein sequence liabilities can be identified by searching for sequence motifs associated with sites containing:

1) Unpaired Cys residues,
2) N-linked glycosylation,
3) Asn deamidation,
4) Asp isomerization,
5) SYE truncation,
6) Met oxidation,
7) Trp oxidation,
8) N-terminal glutamate,
9) Integrin binding,
10) CD11c/CD18 binding, or
11) Fragmentation Such motifs can be eliminated by altering the synthetic gene for the cDNA encoding recombinant antibodies.

Protein engineering efforts in the field of development of therapeutic antibodies clearly reveal that certain sequences or residues are associated with solubility differences (Fernandez-Escamilla et al., *Nature Biotech.*, 22 (10), 1302-1306, 2004; Chennamsetty et al., *PNAS*, 106 (29), 11937-11942, 2009; Voynov et al., *Biocon. Chem.*, 21 (2), 385-392, 2010) Evidence from solubility-altering mutations in the literature indicate that some hydrophilic residues such as aspartic acid, glutamic acid, and serine contribute significantly more favorably to protein solubility than other hydrophilic residues, such as asparagine, glutamine, threonine, lysine, and arginine.

Stability. Antibodies can be engineered for enhanced biophysical properties. One can use elevated temperature to unfold antibodies to determine relative stability, using average apparent melting temperatures. Differential Scanning calorimetry (DSC) measures the heat capacity, $C_p$, of a molecule (the heat required to warm it, per degree) as a function of temperature. One can use DSC to study the thermal stability of antibodies. DSC data for mAbs is particularly interesting because it sometimes resolves the unfolding of individual domains within the mAb structure, producing up to three peaks in the thermogram (from unfolding of the Fab, $C_H2$, and $C_H3$ domains). Typically unfolding of the Fab domain produces the strongest peak. The DSC profiles and relative stability of the Fc portion show characteristic differences for the human $IgG_1$, IgG2, IgG3, and IgG4 subclasses (Garber and Demarest, *Biochem. Biophys. Res. Commun.* 355, 751-757, 2007). One also can determine average apparent melting temperature using circular dichroism (CD), performed with a CD spectrometer. Far-UV CD spectra will be measured for antibodies in the range of 200 to 260 nm at increments of 0.5 nm. The final spectra can be determined as averages of 20 accumulations. Residue ellipticity values can be calculated after background subtraction. Thermal unfolding of antibodies (0.1 mg/mL) can be monitored at 235 nm from 25-95° C. and a heating rate of 1° C./min. One can use dynamic light scattering (DLS) to assess for propensity for aggregation. DLS is used to characterize size of various particles including proteins. If the system is not disperse in size, the mean effective diameter of the particles can be determined. This measurement depends on the size of the particle core, the size of surface structures, and particle concentration. Since DLS essentially measures fluctuations in scattered light intensity due to particles, the diffusion coefficient of the particles can be determined. DLS software in commercial DLA instruments displays the particle population at different diameters. Stability studies can be done conveniently using DLS. DLS measurements of a sample can show whether the particles aggregate over time or with temperature variation by determining whether the hydrodynamic radius of the particle increases. If particles aggregate, one can see a larger population of particles with a larger radius. Stability depending on temperature can be analyzed by controlling the temperature in situ. Capillary electrophoresis (CE) techniques include proven methodologies for determining features of antibody stability. One can use an iCE approach to resolve antibody protein charge variants due to deamidation, C-terminal lysines, sialylation, oxidation, glycosylation, and any other change to the protein that can result in a change in pI of the protein. Each of the expressed antibody proteins can be evaluated by high throughput, free solution isoelectric focusing (IEF) in a capillary column (cIEF), using a Protein Simple Maurice instrument. Whole-column UV absorption detection can be performed every 30 seconds for real time monitoring of molecules focusing at the isoelectric points (pIs). This approach combines the high resolution of traditional gel IEF with the advantages of quantitation and automation found in column-based separations while eliminating the need for a mobilization step. The technique yields reproducible, quantitative analysis of identity, purity, and heterogeneity profiles for the expressed antibodies. The results identify charge heterogeneity and molecular sizing on the antibodies, with both absorbance and native fluorescence detection modes and with sensitivity of detection down to 0.7 µg/mL.

Solubility. One can determine the intrinsic solubility score of antibody sequences. The intrinsic solubility scores can be calculated using CamSol Intrinsic (Sormanni et al., *J Mol Biol* 427, 478-490, 2015). The amino acid sequences for residues 95-102 (Kabat numbering) in HCDR3 of each antibody fragment such as a scFv can be evaluated via the online program to calculate the solubility scores. One also can determine solubility using laboratory techniques. Various techniques exist, including addition of lyophilized protein to a solution until the solution becomes saturated and the solubility limit is reached, or concentration by ultrafiltration in a microconcentrator with a suitable molecular weight cut-off. The most straightforward method is induction of amorphous precipitation, which measures protein solubility using a method involving protein precipitation using ammonium sulfate (Trevino et al., *J Mol Biol*, 366: 449-460, 2007). Ammonium sulfate precipitation gives quick and accurate information on relative solubility values. Ammonium sulfate precipitation produces precipitated solutions with well-defined aqueous and solid phases and requires relatively small amounts of protein. Solubility measurements performed using induction of amorphous precipitation by ammonium sulfate also can be done easily at different pH values. Protein solubility is highly pH dependent, and pH is considered the most important extrinsic factor that affects solubility.

Autoreactivity. Generally, it is thought that autoreactive clones should be eliminated during ontogeny by negative selection, however it has become clear that many human naturally occurring antibodies with autoreactive properties persist in adult mature repertoires, and the autoreactivity may enhance the antiviral function of many antibodies to pathogens. It has been noted that HCDR3 loops in antibodies during early B cell development are often rich in positive charge and exhibit autoreactive patterns (Wardemann et al., *Science* 301, 1374-1377, 2003). One can test a given antibody for autoreactivity by assessing the level of binding to human origin cells in microscopy (using adherent HeLa or HEp-2 epithelial cells) and flow cytometric cell surface staining (using suspension Jurkat T cells and 293S human embryonic kidney cells). Autoreactivity also can be surveyed using assessment of binding to tissues in tissue arrays.

Preferred residues ("Human Likeness"). B cell repertoire deep sequencing of human B cells from blood donors is being performed on a wide scale in many recent studies. Sequence information about a significant portion of the human antibody repertoire facilitates statistical assessment of antibody sequence features common in healthy humans. With knowledge about the antibody sequence features in a human recombined antibody variable gene reference database, the position specific degree of "Human Likeness" (HL) of an antibody sequence can be estimated. HL has been shown to be useful for the development of antibodies in clinical use, like therapeutic antibodies or antibodies as vaccines. The goal is to increase the human likeness of antibodies to reduce potential adverse effects and anti-antibody immune responses that will lead to significantly decreased efficacy of the antibody drug or can induce serious health implications. One can assess antibody characteristics of the combined antibody repertoire of three healthy human blood donors of about 400 million sequences in total and created a novel "relative Human Likeness" (rHL) score that focuses on the hypervariable region of the antibody. The rHL score allows one to easily distinguish between human (positive score) and non-human sequences (negative score). Antibodies can be engineered to eliminate residues that are not common in human repertoires.

D. Single Chain Antibodies

A single chain variable fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma or B cell. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alanine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5\times10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Multispecific Antibodies

In certain embodiments, antibodies of the present disclosure are bispecific or multispecific. Bispecific antibodies are antibodies that have binding specificities for at least two different epitopes. Exemplary bispecific antibodies may bind to two different epitopes of a single antigen. Other such antibodies may combine a first antigen binding site with a binding site for a second antigen. Alternatively, an anti-pathogen arm may be combined with an arm that binds to a triggering molecule on a leukocyte, such as a T-cell receptor molecule (e.g., CD3), or Fc receptors for IgG (FcγR), such as FcγRI (CD64), FcγRII (CD32) and Fc gamma RIII (CD16), so as to focus and localize cellular defense mechanisms to the infected cell. Bispecific antibodies may also be used to localize cytotoxic agents to infected cells. These antibodies possess a pathogen-binding arm and an arm that binds the cytotoxic agent (e.g., saporin, anti-interferon-α, vinca alkaloid, ricin A chain, methotrexate or radioactive isotope hapten). Bispecific antibodies can be prepared as full-length antibodies or antibody fragments (e.g., F(ab')2 bispecific antibodies). WO 96/16673 describes a bispecific anti-ErbB2/anti-Fc gamma RIII antibody and U.S. Pat. No. 5,837,234 discloses a bispecific anti-ErbB2/anti-Fc gamma RI antibody. A bispecific anti-ErbB2/Fc alpha antibody is shown in WO98/02463. U.S. Pat. No. 5,821,337 teaches a bispecific anti-ErbB2/anti-CD3 antibody.

Methods for making bispecific antibodies are known in the art. Traditional production of full-length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of ten different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

According to a different approach, antibody variable regions with the desired binding specificities (antibody-antigen combining sites) are fused to immunoglobulin constant domain sequences. Preferably, the fusion is with an Ig heavy chain constant domain, comprising at least part of the hinge, $C_{H2}$, and $C_{H3}$ regions. It is preferred to have the first heavy-chain constant region ($C_{H1}$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant effect on the yield of the desired chain combination.

In a particular embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_{H3}$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')2 fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Techniques exist that facilitate the direct recovery of Fab'-SH fragments from E. coli, which can be chemically coupled to form bispecific antibodies. Shalaby et al., J. Exp. Med., 175: 217-225 (1992) describe the production of a humanized bispecific antibody F(ab')2 molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described (Merchant et al., Nat. Biotechnol. 16, 677-681 (1998). doi:10.1038/nbt078-677pmid: 9661204). For example, bispecific antibodies have been produced using leucine zippers (Kostelny et al., J. Immunol., 148(5):1547-1553, 1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a $V_H$ connected to a $V_L$ by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

In a particular embodiment, a bispecific or multispecific antibody may be formed as a DOCK-AND-LOCK™ (DNL™) complex (see, e.g., U.S. Pat. Nos. 7,521,056; 7,527,787; 7,534,866; 7,550,143 and 7,666,400, the Examples section of each of which is incorporated herein by reference.) Generally, the technique takes advantage of the specific and high-affinity binding interactions that occur between a dimerization and docking domain (DDD) sequence of the regulatory (R) subunits of cAMP-dependent protein kinase (PKA) and an anchor domain (AD) sequence derived from any of a variety of AKAP proteins (Baillie et al., FEBS Letters. 2005; 579; 3264; Wong and Scott, Nat. Rev. Mol. Cell Biol. 2004; 5: 959). The DDD and AD peptides may be attached to any protein, peptide or other molecule. Because the DDD sequences spontaneously dimerize and bind to the AD sequence, the technique allows the formation of complexes between any selected molecules that may be attached to DDD or AD sequences.

Antibodies with more than two valencies are contemplated. For example, trispecific antibodies can be prepared (Tutt et al., J. Immunol. 147: 60, 1991; Xu et al., Science, 358(6359):85-90, 2017). A multivalent antibody may be internalized (and/or catabolized) faster than a bivalent antibody by a cell expressing an antigen to which the antibodies bind. The antibodies of the present disclosure can be multivalent antibodies with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable regions. For instance, the polypeptide chain(s) may comprise VD1-(X1)$_n$-VD2-(X2)$_n$-Fc, wherein VD1 is a first variable region, VD2 is a second variable region, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable region polypeptides. The multivalent antibody herein may, for instance, comprise from about two to about eight light chain variable region polypeptides. The light chain variable region polypeptides contemplated here comprise a light chain variable region and, optionally, further comprise a $C_L$ domain.

Charge modifications are particularly useful in the context of a multispecific antibody, where amino acid substitutions in Fab molecules result in reducing the mispairing of light chains with non-matching heavy chains (Bence-Jones-type side products), which can occur in the production of Fab-based bi-/multispecific antigen binding molecules with a VH/VL exchange in one (or more, in case of molecules comprising more than two antigen-binding Fab molecules) of their binding arms (see also PCT publication no. WO 2015/150447, particularly the examples therein, incorporated herein by reference in its entirety).

Accordingly, in particular embodiments, an antibody comprised in the therapeutic agent comprises
(a) a first Fab molecule which specifically binds to a first antigen
(b) a second Fab molecule which specifically binds to a second antigen, and wherein the variable domains VL and VH of the Fab light chain and the Fab heavy chain are replaced by each other,
wherein the first antigen is an activating T cell antigen and the second antigen is a target cell antigen, or the first antigen is a target cell antigen and the second antigen is an activating T cell antigen; and
wherein
i) in the constant domain CL of the first Fab molecule under a) the amino acid at position 124 is substituted by a positively charged amino acid (numbering according to Kabat), and wherein in the constant domain CH1 of the first Fab molecule under a) the amino acid at position 147 or the amino acid at position 213 is substituted by a negatively charged amino acid (numbering according to Kabat EU index); or
ii) in the constant domain CL of the second Fab molecule under b) the amino acid at position 124 is substituted by a positively charged amino acid (numbering according to Kabat), and wherein in the constant domain CH1 of the second Fab molecule under b) the amino acid at position 147 or the amino acid at position 213 is substituted by a negatively charged amino acid (numbering according to Kabat EU index).
The antibody may not comprise both modifications mentioned under i) and ii). The constant domains CL and CH1 of the second Fab molecule are not replaced by each other (i.e., remain unexchanged).

In another embodiment of the antibody, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 or the amino acid at position 213 is substituted independently by glutamic acid (E), or aspartic acid (D) (numbering according to Kabat EU index).

In a further embodiment, in the constant domain CL of the first Fab molecule under a) the amino acid at position 124 is substituted independently by lysine (K), arginine (R) or histidine (H) (numbering according to Kabat), and in the constant domain CH1 of the first Fab molecule under a) the amino acid at position 147 is substituted independently by glutamic acid (E), or aspartic acid (D) (numbering according to Kabat EU index).

In a particular embodiment, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)) and the amino acid at position 123 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a more particular embodiment, in the constant domain CL of the first Fab molecule under a) the amino acid at position 124 is substituted by lysine (K) (numbering according to Kabat) and the amino acid at position 123 is substituted by lysine (K) or arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

In an even more particular embodiment, in the constant domain CL of the first Fab molecule under a) the amino acid at position 124 is substituted by lysine (K) (numbering according to Kabat) and the amino acid at position 123 is substituted by arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

F. Chimeric Antigen Receptors

Artificial T cell receptors (also known as chimeric T cell receptors, chimeric immunoreceptors, chimeric antigen receptors (CARs)) are engineered receptors, which graft an arbitrary specificity onto an immune effector cell. Typically, these receptors are used to graft the specificity of a monoclonal antibody onto a T cell, with transfer of their coding sequence facilitated by retroviral vectors. In this way, a large number of target-specific T cells can be generated for adoptive cell transfer. Phase I clinical studies of this approach show efficacy.

The most common form of these molecules are fusions of single-chain variable fragments (scFv) derived from monoclonal antibodies, fused to CD3-zeta transmembrane and endodomain. Such molecules result in the transmission of a zeta signal in response to recognition by the scFv of its target. An example of such a construct is 14g2a-Zeta, which is a fusion of a scFv derived from hybridoma 14g2a (which recognizes disialoganglioside GD2). When T cells express this molecule (usually achieved by oncoretroviral vector transduction), they recognize and kill target cells that express GD2 (e.g., neuroblastoma cells). To target malignant B cells, investigators have redirected the specificity of T cells using a chimeric immunoreceptor specific for the B-lineage molecule, CD19.

The variable portions of an immunoglobulin heavy and light chain are fused by a flexible linker to form a scFv. This scFv is preceded by a signal peptide to direct the nascent protein to the endoplasmic reticulum and subsequent surface expression (this is cleaved). A flexible spacer allows to the scFv to orient in different directions to enable antigen binding. The transmembrane domain is a typical hydrophobic alpha helix usually derived from the original molecule of the signaling endodomain which protrudes into the cell and transmits the desired signal.

Type I proteins are in fact two protein domains linked by a transmembrane alpha helix in between. The cell membrane lipid bilayer, through which the transmembrane domain passes, acts to isolate the inside portion (endodomain) from the external portion (ectodomain). It is not so surprising that attaching an ectodomain from one protein to an endodomain of another protein results in a molecule that combines the recognition of the former to the signal of the latter.

Ectodomain. A signal peptide directs the nascent protein into the endoplasmic reticulum. This is essential if the receptor is to be glycosylated and anchored in the cell membrane. Any eukaryotic signal peptide sequence usually works fine. Generally, the signal peptide natively attached to the amino-terminal most component is used (e.g., in a scFv with orientation light chain—linker—heavy chain, the native signal of the light-chain is used The antigen recognition domain is usually an scFv. There are however many alternatives. An antigen recognition domain from native T-cell receptor (TCR) alpha and beta single chains have been described, as have simple ectodomains (e.g., CD4 ectodomain to recognize HIV infected cells) and more exotic recognition components such as a linked cytokine (which leads to recognition of cells bearing the cytokine receptor). In fact, almost anything that binds a given target with high affinity can be used as an antigen recognition region.

A spacer region links the antigen binding domain to the transmembrane domain. It should be flexible enough to allow the antigen binding domain to orient in different directions to facilitate antigen recognition. The simplest form is the hinge region from IgG1. Alternatives include the $CH_2CH_3$ region of immunoglobulin and portions of CD3. For most scFv based constructs, the IgG1 hinge suffices. However, the best spacer often has to be determined empirically.

Transmembrane domain. The transmembrane domain is a hydrophobic alpha helix that spans the membrane. Generally, the transmembrane domain from the most membrane proximal component of the endodomain is used. Interestingly, using the CD3-zeta transmembrane domain may result in incorporation of the artificial TCR into the native TCR a factor that is dependent on the presence of the native CD3-zeta transmembrane charged aspartic acid residue. Different transmembrane domains result in different receptor stability. The CD28 transmembrane domain results in a brightly expressed, stable receptor.

Endodomain. This is the "business-end" of the receptor. After antigen recognition, receptors cluster and a signal is transmitted to the cell. The most commonly used endodomain component is CD3-zeta which contains 3 ITAMs. This transmits an activation signal to the T cell after antigen is bound. CD3-zeta may not provide a fully competent activation signal and additional co-stimulatory signaling is needed.

"First-generation" CARs typically had the intracellular domain from the CD3ξ-chain, which is the primary transmitter of signals from endogenous TCRs. "Second-generation" CARs add intracellular signaling domains from various costimulatory protein receptors (e.g., CD28, 41BB, ICOS) to the cytoplasmic tail of the CAR to provide additional signals to the T cell. Preclinical studies have indicated that the second generation of CAR designs improves the antitumor activity of T cells. More recent, "third-generation" CARs combine multiple signaling domains, such as CD3z-CD28-41BB or CD3z-CD28-OX40, to further augment potency.

G. ADCs

Antibody Drug Conjugates or ADCs are a new class of highly potent biopharmaceutical drugs designed as a targeted therapy for the treatment of people with infectious disease. ADCs are complex molecules composed of an antibody (a whole mAb or an antibody fragment such as a single-chain variable fragment, or scFv) linked, via a stable chemical linker with labile bonds, to a biological active cytotoxic/anti-viral payload or drug. Antibody Drug Conjugates are examples of bioconjugates and immunoconjugates.

By combining the unique targeting capabilities of monoclonal antibodies with the cancer-killing ability of cytotoxic drugs, antibody-drug conjugates allow sensitive discrimination between healthy and diseased tissue. This means that, in contrast to traditional systemic approaches, antibody-drug conjugates target and attack the infected cell so that healthy cells are less severely affected.

In the development ADC-based anti-tumor therapies, an anticancer drug (e.g., a cell toxin or cytotoxin) is coupled to an antibody that specifically targets a certain cell marker (e.g., a protein that, ideally, is only to be found in or on infected cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cell or impairs viral replication. Due to this targeting, ideally the drug has lower side effects and gives a wider therapeutic window than other agents.

A stable link between the antibody and cytotoxic/antiviral agent is a crucial aspect of an ADC. Linkers are based on chemical motifs including disulfides, hydrazones or peptides (cleavable), or thioethers (noncleavable) and control the distribution and delivery of the cytotoxic agent to the target cell. Cleavable and noncleavable types of linkers have been proven to be safe in preclinical and clinical trials. Brentuximab vedotin includes an enzyme-sensitive cleavable linker that delivers the potent and highly toxic antimicrotubule agent Monomethyl auristatin E or MMAE, a synthetic antineoplastic agent, to human specific CD30-positive malignant cells. Because of its high toxicity MMAE, which inhibits cell division by blocking the polymerization of tubulin, cannot be used as a single-agent chemotherapeutic drug. However, the combination of MMAE linked to an anti-CD30 monoclonal antibody (cAC10, a cell membrane protein of the tumor necrosis factor or TNF receptor) proved to be stable in extracellular fluid, cleavable by cathepsin and safe for therapy. Trastuzumab emtansine, the other approved ADC, is a combination of the microtubule-formation inhibitor mertansine (DM-1), a derivative of the Maytansine, and antibody trastuzumab (Herceptin®/Genentech/Roche) attached by a stable, non-cleavable linker. The availability of better and more stable linkers has changed the function of the chemical bond. The type of linker, cleavable or noncleavable, lends specific properties to the cytotoxic (anti-cancer) drug. For example, a non-cleavable linker keeps the drug within the cell. As a result, the entire antibody, linker and cytotoxic agent enter the targeted cancer cell where the antibody is degraded to the level of an amino acid. The resulting complex—amino acid, linker and cytotoxic agent—now becomes the active drug. In contrast, cleavable linkers are catalyzed by enzymes in the host cell where it releases the cytotoxic agent.

Another type of cleavable linker, currently in development, adds an extra molecule between the cytotoxic/antiviral drug and the cleavage site. This linker technology allows researchers to create ADCs with more flexibility without worrying about changing cleavage kinetics. Researchers are also developing a new method of peptide cleavage based on Edman degradation, a method of sequencing amino acids in a peptide. Future direction in the development of ADCs also include the development of site-specific conjugation (TDCs) to further improve stability and therapeutic index and a emitting immunoconjugates and antibody-conjugated nanoparticles.

H. BiTES

Bi-specific T-cell engagers (BiTEs) are a class of artificial bispecific monoclonal antibodies that are investigated for the use as anti-cancer drugs. They direct a host's immune system, more specifically the T cells' cytotoxic activity, against infected cells. BiTE is a registered trademark of Micromet AG.

BiTEs are fusion proteins consisting of two single-chain variable fragments (scFvs) of different antibodies, or amino acid sequences from four different genes, on a single peptide chain of about 55 kilodaltons. One of the scFvs binds to T cells via the CD3 receptor, and the other to an infected cell via a specific molecule.

Like other bispecific antibodies, and unlike ordinary monoclonal antibodies, BiTEs form a link between T cells and target cells. This causes T cells to exert cytotoxic/antiviral activity on infected cells by producing proteins like perforin and granzymes, independently of the presence of MHC I or co-stimulatory molecules. These proteins enter infected cells and initiate the cell's apoptosis. This action mimics physiological processes observed during T cell attacks against infected cells.

I. Intrabodies

In a particular embodiment, the antibody is a recombinant antibody that is suitable for action inside of a cell—such antibodies are known as "intrabodies." These antibodies may interfere with target function by a variety of mechanism, such as by altering intracellular protein trafficking, interfering with enzymatic function, and blocking protein-protein or protein-DNA interactions. In many ways, their structures mimic or parallel those of single chain and single domain antibodies, discussed above. Indeed, single-transcript/single-chain is an important feature that permits intracellular expression in a target cell, and also makes protein transit across cell membranes more feasible. However, additional features are required.

The two major issues impacting the implementation of intrabody therapeutic are delivery, including cell/tissue targeting, and stability. With respect to delivery, a variety of approaches have been employed, such as tissue-directed delivery, use of cell-type specific promoters, viral-based delivery and use of cell-permeability/membrane translocating peptides. With respect to the stability, the approach is generally to either screen by brute force, including methods that involve phage display and may include sequence maturation or development of consensus sequences, or more directed modifications such as insertion stabilizing sequences (e.g., Fc regions, chaperone protein sequences, leucine zippers) and disulfide replacement/modification.

An additional feature that intrabodies may require is a signal for intracellular targeting. Vectors that can target intrabodies (or other proteins) to subcellular regions such as the cytoplasm, nucleus, mitochondria and ER have been designed and are commercially available (Invitrogen Corp.; Persic et al., 1997).

By virtue of their ability to enter cells, intrabodies have additional uses that other types of antibodies may not achieve. In the case of the present antibodies, the ability to interact with the MUC1 cytoplasmic domain in a living cell may interfere with functions associated with the MUC1 CD, such as signaling functions (binding to other molecules) or oligomer formation. In particular, it is contemplated that such antibodies can be used to inhibit MUC1 dimer formation.

J. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies are bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

III. Active/Passive Immunization and Treatment/Prevention of Yellow Fever Virus Infection A. Formulation and Administration The present disclosure provides pharmaceutical compositions comprising anti-YFV antibodies and antigens for generating the same. Such compositions comprise a prophylactically or therapeutically effective amount of an antibody or a fragment thereof, or a peptide immunogen, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, intrarectal, vaginal, topical or delivered by mechanical ventilation.

Active vaccines are also envisioned where antibodies like those disclosed are produced in vivo in a subject at risk of YFV infection. Such vaccines can be formulated for parenteral administration, e.g., formulated for injection via the intradermal, intravenous, intramuscular, subcutaneous, or even intraperitoneal routes. Administration by intradermal and intramuscular routes are contemplated. The vaccine could alternatively be administered by a topical route directly to the mucosa, for example, by nasal drops, inhalation, by nebulizer, or via intrarectal or vaginal delivery. Pharmaceutically acceptable salts include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Passive transfer of antibodies, known as artificially acquired passive immunity, generally will involve the use of intravenous or intramuscular injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAb). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

2. ADCC

Antibody-dependent cell-mediated cytotoxicity (ADCC) is an immune mechanism leading to the lysis of antibody-coated target cells by immune effector cells. The target cells are cells to which antibodies or fragments thereof comprising an Fc region specifically bind, generally via the protein part that is N-terminal to the Fc region. By "antibody having increased/reduced antibody dependent cell-mediated cytotoxicity (ADCC)" is meant an antibody having increased/reduced ADCC as determined by any suitable method known to those of ordinary skill in the art.

As used herein, the term "increased/reduced ADCC" is defined as either an increase/reduction in the number of target cells that are lysed in a given time, at a given concentration of antibody in the medium surrounding the target cells, by the mechanism of ADCC defined above, and/or a reduction/increase in the concentration of antibody, in the medium surrounding the target cells, required to achieve the lysis of a given number of target cells in a given time, by the mechanism of ADCC. The increase/reduction in ADCC is relative to the ADCC mediated by the same antibody produced by the same type of host cells, using the same standard production, purification, formulation and storage methods (which are known to those skilled in the art), but that has not been engineered. For example, the increase in ADCC mediated by an antibody produced by host cells engineered to have an altered pattern of glycosylation (e.g., to express the glycosyltransferase, GnTIII, or other glycosyltransferases) by the methods described herein, is relative to the ADCC mediated by the same antibody produced by the same type of non-engineered host cells.

3. CDC

Complement-dependent cytotoxicity (CDC) is a function of the complement system. It is the processes in the immune system that kill pathogens by damaging their membranes without the involvement of antibodies or cells of the immune system. There are three main processes. All three insert one or more membrane attack complexes (MAC) into the pathogen which cause lethal colloid-osmotic swelling, i.e., CDC. It is one of the mechanisms by which antibodies or antibody fragments have an anti-viral effect.

IV. Antibody Conjugates

Antibodies of the present disclosure may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{152}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Additional types of antibodies contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850,752, 3,939, 350, 3,996,345, 4,277,437, 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. Immunodetection Methods

In still further embodiments, the present disclosure concerns immunodetection methods for binding, purifying, removing, quantifying and otherwise generally detecting YFV and its associated antigens. While such methods can be applied in a traditional sense, another use will be in quality control and monitoring of vaccine and other virus stocks, where antibodies according to the present disclosure can be used to assess the amount or integrity (i.e., long term stability) of antigens in viruses. Alternatively, the methods may be used to screen various antibodies for appropriate/desired reactivity profiles.

Other immunodetection methods include specific assays for determining the presence of YFV in a subject. A wide variety of assay formats are contemplated, but specifically those that would be used to detect YFV in a fluid obtained from a subject, such as saliva, blood, plasma, sputum, semen or urine. In particular, semen has been demonstrated as a viable sample for detecting YFV (Purpura et al., 2016; Mansuy et al., 2016; Barzon et al., 2016; Gornet et al., 2016; Duffy et al., 2009; CDC, 2016; Halfon et al., 2010; Elder et al. 2005). The assays may be advantageously formatted for non-healthcare (home) use, including lateral flow assays (see below) analogous to home pregnancy tests. These assays may be packaged in the form of a kit with appropriate reagents and instructions to permit use by the subject of a family member.

Some immunodetection methods include enzyme linked immunosorbent assay (ELISA), radioimmunoas say (RIA), immunoradiometric assay, fluoroimmunoassay, chemiluminescent assay, bioluminescent assay, and Western blot to mention a few. In particular, a competitive assay for the detection and quantitation of YFV antibodies directed to specific parasite epitopes in samples also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing YFV, and contacting the sample with a first antibody in accordance with the present disclosure, as the case may be, under conditions effective to allow the formation of immunocomplexes.

These methods include methods for purifying YFV or related antigens from a sample. The antibody will preferably be linked to a solid support, such as in the form of a column matrix, and the sample suspected of containing the YFV or antigenic component will be applied to the immobilized antibody. The unwanted components will be washed from the column, leaving the YFV antigen immunocomplexed to the immobilized antibody, which is then collected by removing the organism or antigen from the column.

The immunobinding methods also include methods for detecting and quantifying the amount of YFV or related components in a sample and the detection and quantification of any immune complexes formed during the binding process. Here, one would obtain a sample suspected of containing YFV or its antigens and contact the sample with an antibody that binds YFV or components thereof, followed by detecting and quantifying the amount of immune complexes formed under the specific conditions. In terms of antigen detection, the biological sample analyzed may be any sample that is suspected of containing YFV or YFV antigen, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to YFV or antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, for example, with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the YFV or YFV antigen is added to the wells. After binding and washing to remove non-specifically bound immune complexes, the bound antigen may be detected. Detection may be achieved by the addition of another anti-YFV antibody that is linked to a detectable label. This type of ELISA is a simple "sandwich ELISA." Detection may also be achieved by the addition of a second anti-YFV antibody, followed by the addition of a third antibody that has binding affinity for the second antibody, with the third antibody being linked to a detectable label.

In another exemplary ELISA, the samples suspected of containing the YFV or YFV antigen are immobilized onto the well surface and then contacted with the anti-YFV antibodies of the disclosure. After binding and washing to remove non-specifically bound immune complexes, the bound anti-YFV antibodies are detected. Where the initial anti-YFV antibodies are linked to a detectable label, the immune complexes may be detected directly. Again, the immune complexes may be detected using a second antibody that has binding affinity for the first anti-YFV antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present disclosure contemplates the use of competitive formats. This is particularly useful in the detection of YFV antibodies in sample. In competition-based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventor proposes the use of labeled YFV monoclonal antibodies to determine the amount of YFV antibodies in a sample. The basic format would include contacting a known amount of YFV monoclonal antibody (linked to a detectable label) with YFV antigen or particle. The YFV antigen or organism is preferably attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Lateral Flow Assays

Lateral flow assays, also known as lateral flow immunochromatographic assays, are simple devices intended to detect the presence (or absence) of a target analyte in sample (matrix) without the need for specialized and costly equipment, though many laboratory-based applications exist that are supported by reading equipment. Typically, these tests are used as low resources medical diagnostics, either for home testing, point of care testing, or laboratory use. A widely spread and well-known application is the home pregnancy test.

The technology is based on a series of capillary beds, such as pieces of porous paper or sintered polymer. Each of these elements has the capacity to transport fluid (e.g., urine) spontaneously. The first element (the sample pad) acts as a sponge and holds an excess of sample fluid. Once soaked, the fluid migrates to the second element (conjugate pad) in which the manufacturer has stored the so-called conjugate, a dried format of bio-active particles (see below) in a salt-sugar matrix that contains everything to guarantee an optimized chemical reaction between the target molecule (e.g., an antigen) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these strips, analyte has been bound on the particle and the third 'capture' molecule binds the complex. After a while, when more and more fluid has passed the stripes, particles accumulate and the stripe-area changes color. Typically there are at least two stripes: one (the control) that captures any particle and thereby shows that reaction conditions and technology worked fine, the second contains a specific capture molecule and only captures those particles onto which an analyte molecule has been immobilized. After passing these reaction zones, the fluid enters the final porous material—the wick—that simply acts as a waste container. Lateral Flow Tests can operate as either competitive or sandwich assays. Lateral flow assays are disclosed in U.S. Pat. No. 6,485,982.

D. Immunohistochemistry

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

E. Immunodetection Kits

In still further embodiments, the present disclosure concerns immunodetection kits for use with the immunodetection methods described above. As the antibodies may be used to detect YFV or YFV antigens, the antibodies may be included in the kit. The immunodetection kits will thus comprise, in suitable container means, a first antibody that binds to YFV or YFV antigen, and optionally an immunodetection reagent.

In certain embodiments, the YFV antibody may be pre-bound to a solid support, such as a column matrix and/or well of a microtiter plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of the YFV or YFV antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

F. Vaccine and Antigen Quality Control Assays

The present disclosure also contemplates the use of antibodies and antibody fragments as described herein for use in assessing the antigenic integrity of a viral antigen in a sample. Biological medicinal products like vaccines differ from chemical drugs in that they cannot normally be characterized molecularly; antibodies are large molecules of significant complexity and have the capacity to vary widely from preparation to preparation. They are also administered to healthy individuals, including children at the start of their lives, and thus a strong emphasis must be placed on their quality to ensure, to the greatest extent possible, that they are efficacious in preventing or treating life-threatening disease, without themselves causing harm.

The increasing globalization in the production and distribution of vaccines has opened new possibilities to better manage public health concerns but has also raised questions about the equivalence and interchangeability of vaccines procured across a variety of sources. International standardization of starting materials, of production and quality control testing, and the setting of high expectations for regulatory oversight on the way these products are manufactured and used, have thus been the cornerstone for continued success. But it remains a field in constant change, and continuous technical advances in the field offer a promise of developing potent new weapons against the oldest public health threats, as well as new ones—malaria, pandemic influenza, and HIV, to name a few—but also put a great pressure on manufacturers, regulatory authorities, and the wider medical community to ensure that products continue to meet the highest standards of quality attainable.

Thus, one may obtain an antigen or vaccine from any source or at any point during a manufacturing process. The quality control processes may therefore begin with preparing a sample for an immunoassay that identifies binding of an antibody or fragment disclosed herein to a viral antigen. Such immunoassays are disclosed elsewhere in this document, and any of these may be used to assess the structural/antigenic integrity of the antigen. Standards for finding the sample to contain acceptable amounts of antigenically correct and intact antigen may be established by regulatory agencies.

Another important embodiment where antigen integrity is assessed is in determining shelf-life and storage stability. Most medicines, including vaccines, can deteriorate over time. Therefore, it is critical to determine whether, over time, the degree to which an antigen, such as in a vaccine, degrades or destabilizes such that is it no longer antigenic and/or capable of generating an immune response when administered to a subject. Again, standards for finding the sample to contain acceptable amounts of antigenically intact antigen may be established by regulatory agencies.

In certain embodiments, viral antigens may contain more than one protective epitope. In these cases, it may prove useful to employ assays that look at the binding of more than one antibody, such as 2, 3, 4, 5 or even more antibodies. These antibodies bind to closely related epitopes, such that they are adjacent or even overlap each other. On the other hand, they may represent distinct epitopes from disparate parts of the antigen. By examining the integrity of multiple epitopes, a more complete picture of the antigen's overall integrity, and hence ability to generate a protective immune response, may be determined.

Antibodies and fragments thereof as described in the present disclosure may also be used in a kit for monitoring the efficacy of vaccination procedures by detecting the presence of protective YFV antibodies. Antibodies, antibody fragment, or variants and derivatives thereof, as described in the present disclosure may also be used in a kit for monitoring vaccine manufacture with the desired immunogenicity.

VI. Examples

The following examples are included to demonstrate preferred embodiments. It should be appreciated by those of skill in the art that the techniques disclosed in the examples that follow represent techniques discovered by the inventor to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Generation of human monoclonal antibodies. Blood samples were obtained after written informed consent from four human subjects aged 20 to 47 years who were previously vaccinated with a YFV vaccine prior to travel. The studies were reviewed and approved by the Institutional Review Board of Vanderbilt University Medical Center. Peripheral blood mononuclear cells (PBMCs) were isolated from whole blood and transformed using Epstein-Barr virus (EBV), as previously described (Smith and Crowe, 2015). Briefly, transformed B cells were expanded and co-cultured with irradiated human PBMCs in 96-well plates. Cell supernatants were screened by ELISA using recombinant YFV E protein (Meridian Life Sciences). Wells with positive reactivity were fused to a human-mouse myeloma cell line (HMMA 2.5) and plated by limiting dilution in 384-well plates. The resulting hybridomas were cloned by fluorescence-activated cell sorting (FACS) to produce clonal hybridoma cell lines. These clonal hybridoma cells were cultured in T-225 flasks containing serum-free medium, and mAb was purified from spent medium by affinity chromatography on an ÄKTA™ pure Fast Protein Liquid Chromatography (FPLC) instrument (Cytiva).

Recombinant antibody expression and purification. For animal studies, large-scale recombinant antibody production of YFV-136 was performed. RNA was isolated from YFV-136 hybridoma line, and heavy and light chain genes were amplified using 5□RACE (Rapid Amplification of cDNA Ends) and sequenced using a Pacific Biosciences Sequel instrument. Variable regions of YFV-136 were cloned into a monocistronic full-length, human IgG1 expression vector (Twist Biosciences) for recombinant production. This expression vector then was transfected transiently into ExpiCHO cells for 7 to 8 days. Cell supernatants were harvested and filtered through 0.45-µm filters prior to purification. Purification was performed on an ÄKTA™ pure Fast Protein Liquid Chromatography (FPLC) instrument (Cytiva) using HiTrap MabSelect SuRe columns (Cytiva) as described above for hybridoma-derived mAbs.

ELISA binding of mAbs to YFV E protein. 384-well plates were coated with 2 µg/mL of YFV E protein (Meridian Life Science) at 25 µL/well and incubated overnight at 4° C. Plates then were washed and blocked using Dulbecco's PBS with Tween 20 (DPBS-T) containing 2% milk and 1% goat serum for 1 hr at room temperature. Following a wash step, serial dilutions of antibody in DPBS were added to plates and incubated for 1 hr at room temperature. To detect bound antibodies, alkaline phosphatase conjugated goat anti-human IgG diluted 1:4,000 in DPBS-T containing 1% milk and 1% goat serum was added to plates for 1 hr at room temperature and developed using AP substrate tablets diluted in 1 M Tris, 0.3 mM magnesium chloride. Plates were developed in the dark for 1 hr and read on a BioTek plate reader at 405 nm. Binding curves were interpolated in Prism software (GraphPad) using a non-linear regression analysis.

YFV-17D focus reduction neutralization test (FRNT). A focus reduction neutralization test was performed as previously described with minor amendments. Briefly, 96-well plates were seeded with Vero cells at $2.5 \times 10^4$ cells/well and incubated overnight. The following day, serial dilutions of antibody were mixed with $10^2$ FFU YFV-17D and incubated at 37° C. for 1 hr. 30 µL/well of virus/antibody mixture then was added to Vero cell culture monolayers and incubated at 37° C. for 1 hr. Without washing, 110 µL per well of overlay containing a 1:1 mixture of 2.4% methylcellulose and 2× Dulbecco's Modified Eagle Medium (DMEM) with 4% FBS was added to plates, which then were incubated for 72 hr at 37° C. in 5% $CO_2$. To stain foci of virus infection, cells were fixed with 1% paraformaldehyde for 1 hr at room temperature, washed, and permeabilized using permeabilization buffer (0.1% saponin, 0.1% BSA in DPBS) for 10 min. Cells then were stained with 1 µg/mL of pan-flavivirus murine mAb 4G2 in permeabilization buffer for 1 hr at room temperature. After two washes, goat anti-mouse IgG-horseradish peroxidase (Southern Biotech) diluted 1:1,000 in permeabilization buffer was added to cells and incubated for 1 hr at room temperature. Foci were developed using TrueBlue peroxidase and counted using a spot counter instrument (ImmunoSpot; CTL). Foci counts were normalized to that of a virus-only control, and neutralization curves were interpolated in Prism software using a non-linear regression analysis.

Virulent and 17D YFV strain FRNT. FRNT was performed as described above, with the following exceptions: 100 µL containing 200 FFU of virus was mixed with 100 µL of serially-diluted mAb and incubated at 37° C. for 1 hr. 100 µL of virus:mAb mixture was then added to Vero cells in 96-well plate format and incubated at 37° C. for 1 hr, and followed by addition of overlay and incubation at 37° C. for two days. Cells were then fixed with 4% paraformaldehyde (final concentration) for 30 min, permeabilized, stained, and analyzed as described above.

Pre- and post-attachment neutralization of YFV-17D. Pre- and post-attachment neutralization assays were performed as previously described (Williamson et al., 2020). For pre-attachment studies, 600 FFU YFV-17D was mixed with serial dilutions of antibody for 1 hr at 37° C. Cells and virus/mAb mixtures were then pre-chilled for 15 min prior to addition of mixtures to cell monolayers for 1 hr at 4° C. Cells then were washed three times and incubated with pre-warmed DMEM for 15 min prior to addition of methylcellulose overlay containing DMEM. For post-attachment studies, cell monolayers first were incubated with virus for 1 hr at 4° C. Cells then were washed and incubated with serial dilutions of antibody for 1 hr at 4° C. Excess antibody then was washed off, and cells were incubated for 15 min at 37° C. with DMEM prior to addition of overlay. Foci were enumerated as described for the focus reduction neutralization test described above.

Biolayer interferometry competition-binding assay. Competition-binding studies were performed using a biolayer interferometry instrument (ForteBio Octet® HTX). HIS 1K sensortips were pre-incubated in kinetics buffer (Pall) for 10 min. After a 60 sec baseline step, his-tagged YFV E protein (Meridian Life Science) was associated to the tips at 5 µg/mL for 60 sec. Readings again were set to baseline for 60 sec, followed by association of the first antibody at 25 µg/mL for 600 sec to achieve complete saturation. Tip readings again were baselined, and then tips were dipped into wells containing a second antibody at 25 µg/mL for 180 sec. Data were analyzed using ForteBio data analysis software. Data from all steps were normalized to a buffer-only control, and antibodies were grouped using a Pearson correlation statistical analysis.

Generation and analysis of YFV-17D escape mutations. In a U-bottom 96 well plate, 25 µL mAb YFV-136 IgG protein at 5 µg/mL was pre-mixed with 25 µL YFV-17D virus (Breit et al., 1993) diluted 1:10 (5,000 FFU) in DMEM without FBS and incubated for 1 hr at 37° C. This procedure was done in 16 separate wells within the 96-well plate. Virus also was mixed with DMEM alone and passaged throughout the study to control for substitutions that arise from cell culture adaptation. 50 µL virus/antibody mixture and controls were added to HuH-7.5 cell culture monolayers in 96-well ePlates (Agilent) and incubated for 1 hr at 37° C. 100 µL of DMEM containing 5% FBS was then added to each well, plates placed back on an xCELLigence instrument (Agilent), and cell monolayers were monitored for delayed CPE. Cell supernatants in wells with a delayed CPE phenotype, as well as a virus-only control, were subjected to a repeat of this assay to confirm viral escape. Once escape was confirmed, 6-well plates containing confluent Huh7.5 cell monolayers were inoculated with 100 µL/well escape virus or a virus control in the presence of 10 µg/mL of YFV-136 for outgrowth of escape virus. Virus was harvested from 6-well plates, and RNA isolated using the Qiagen virus RNA isolation kit. E and prM genes from isolated RNA were reverse-transcribed to cDNA and PCR-amplified using primers flanking the prM and E genes (One-step RT-PCR kit). Genes then were sequenced by GENEWIZ using overlapping primers that give coverage across prM and E. The control virus sequence was aligned to the 17D reference genome sequence to confirm that mutations did not result from adaptation to cell culture.

Syrian golden hamster YFV strain Jimenez challenge studies. The Syrian golden hamster model used for these studies has been described previously (Julander et al., 2014). Thirty female Syrian golden hamsters (LVG/Lak strain) supplied by Charles River were used. Hamsters were randomized by weight to experimental groups and individually marked with ear tags. For challenge studies, hamsters were challenged at day 0 with 200 of 50% cell culture infectious doses ($CCID_{50}$) hamster-adapted YFV Jimenez strain by bilateral intraperitoneal injections in a total of 0.2 mL. At 3 days post-virus inoculation, hamsters were dosed at 50 mg/kg of recombinant YFV-136 (rYFV-136) (1 mL total volume) or 10 mg/kg of rDENV-2D22 control and monitored for weight loss and clinical manifestations for 21 days. Blood samples were taken at days 4 and 6 to assess viremia and ALT. Any surviving animals were humanely euthanized at the experimental endpoint.

Measurement of hamster serum aminotransferase. ALT (SGPT) reagent (Teco Diagnostics, Anaheim, Calif.) was used, and the protocol was altered for use in 96-well plates. Briefly, 50 µL aminotransferase substrate was placed in each well of a 96-well plate, and 15 µL of sample was added at timed intervals. The samples were incubated at 37° C., after which 50 µL color reagent was added to each sample and incubated for 10 min as above. A volume of 200 µL of color developer was next added to each well and incubated for 5 min. The plate was then read on a spectrophotometer, and aminotransferase concentrations were determined per manufacturer's instructions.

50% cell culture infectious doses ($CCID_{50}$) assays to assess hamster viral burdens. Virus titer was quantified using an infectious cell culture assay in which a volume of either tissue homogenate or serum was added to the first tube of a series of dilution tubes. Serial dilutions were made and added to Vero cell monolayer cultures. Ten days later, CPE was used to identify the endpoint of infection. Four replicates were used to calculate the $CCID_{50}$ of virus per mL of plasma or gram of tissues.

Mouse studies. All mouse experiments were conducted under a Washington University School of Medicine Institutional Animal Care and Use Committee approved protocol in compliance with the Animal Welfare Act. Female hFRG mice were generated by Yecuris Corporation and maintained according to their specific care and use guidelines (see Bailey et al., 2020, for additional details). Only mice with human albumin levels of ≥5.0 mg/mL in plasma (indicative of ≥70% engraftment) were used for this study. hFRG mice were continued on their regular diet of PicoLab High Energy Mouse Diet, 5LJ5 chow (LabDiet) and 3.25% w/v dextrose-water during infection experiments. Mice were inoculated with via retro-orbital injection of 50 µL containing 2×10⁵ FFU wt YFV-Dakar, obtained from the World Reference Center for Emerging Viruses and Arboviruses and passaged once in Vero-CCL81 cells. Antibodies were given as a single treatment of 10 mg/kg dose, diluted in PBS in a 100 µL total volume and given by the i.p. route, 8 hrs post-infection. The DENV2D22 mAb was used as a control. Euthanasia was performed via ketamine overdose and thoracotomy. Blood was collected via aspiration from the cardiac chambers and PT was measured on a Coagucheck (Roche). Perfusion of the entire vascular tree was then performed with saline prior to liver collection. After centrifugation, serum was mixed 1:9 with 10% Triton X-100 in HBSS (1% final volume of Triton-X-100), then incubated at room temperature for 1 h to inactivate infectious virus (Bailey et al., 2020). ALT, bilirubin, and ammonia were analyzed using the Catalyst Dx Chemistry Analyzer (IDEXX Laboratories). Some specimens required dilutions to achieve an ALT value within the analytical measurement range; in these instances, dilution was performed in HBSS and the value was corrected by the final dilution factor. RNA extraction and viral load analysis was performed as described previously (Bailey et al., 2020) using the KingFisher Flex (Thermo Fisher) and the TaqMan RNA-to-CT 1-Step Kit (Thermo Fisher) on the QuantStudio 6 Flex Real-Time PCR System with the following primers: F: 5'-AGGTGCATTGGTCTGCAAAT-3' (SEQ ID NO:19); R: 5'-TCTCTGCTAATCGCTCAAIG-3' (SEQ ID NO:20); P: 5'-/56-FAM/GTTGCTAGGCAATAAACACATTTGGA/3BHQ_1/-3' (SEQ ID NO:21).

Example 2—Results

Figure 1A:
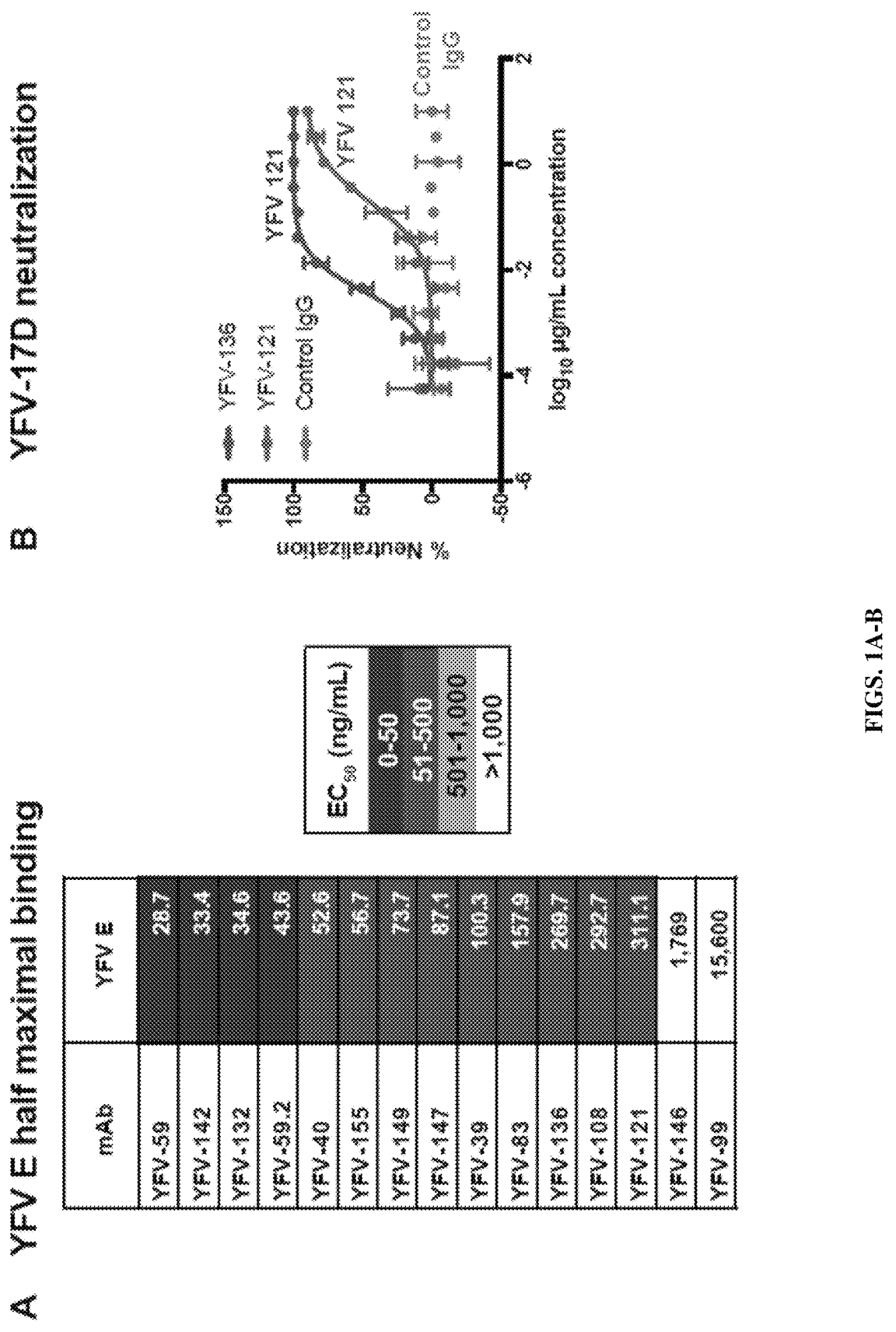

Isolation of monoclonal antibodies from YFV vaccine recipients. Peripheral blood mononuclear cells (PBMCs) from subjects who received a YFV vaccine previously (varying from months to years prior) were transformed in vitro with Epstein-Barr virus (EBV) to screen for YFV-reactive antibodies secreted by transformed memory B cells. The inventor screened cell supernatants for binding to recombinant YFV E protein by ELISA and/or binding to YFV-17D-infected cells by flow cytometry. Cells secreting YFV-reactive antibodies were fused to a myeloma partner to generate hybridoma lines, which were cloned by flow cytometric cell sorting. Antibody was purified from serum-free hybridoma cell line supernatants by affinity chromatography. Using these methods, the inventor isolated 15 mAbs from four YFV-immune subjects. These antibodies bound to recombinant E protein by ELISA with varying half maximal effective concentrations (EC50) for binding ranging from 29 to 15,600 ng/mL (FIG. 1A).

Figure 2A:
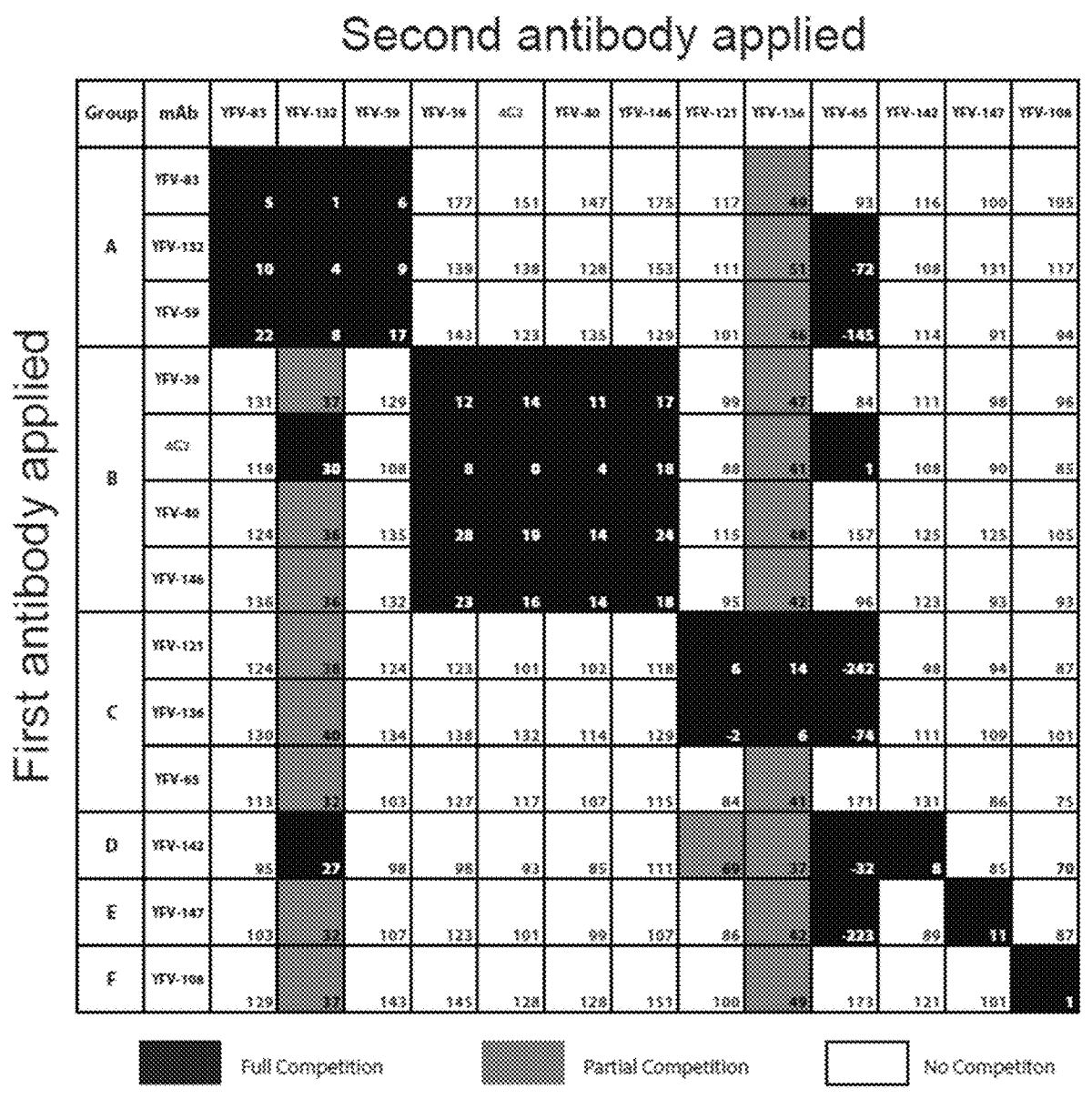

Competition-binding reveals antibodies target several antigenic sites on the E protein. The inventor used high-throughput biolayer interferometry (BLI) to perform competition-binding studies that enable grouping of antibodies based on the major antigenic sites recognized (FIG. 2A). In this platform, antigen is loaded onto a biosensor tip, with two antibodies sequentially flowed over the tip. If mAbs recognize non-overlapping antigenic sites, both bind to the coated sensors when applied in sequence. If binding of the first antibody applied to the antigen-coated sensor reduces or prevents binding of the second antibody, the pair of mAbs likely bind to the same or an overlapping antigenic site. The inventor included the previously described pan-flavivirus reactive murine mAb 4G2 targeting the fusion loop (FL) for comparison. The human antibodies recognized five major antigenic sites. One group of mAbs, including YFV-39, -40, and -146, competed for binding with 4G2, indicating that these mAbs target regions near the FL epitope on YFV E. The neutralizing mAbs YFV-121 and -136 grouped together, indicating these mAbs target an overlapping antigenic site of neutralization vulnerability on YFV E. YFV-65 also competed for binding to E with YFV-121 and YFV-136, even though it did not neutralize YFV-17D when tested at concentrations as high as 10 µg/mL. These data suggest there are multiple antigenic sites on YFV E, with at least one site being a target of potently neutralizing antibodies.

Neutralization of vaccine and pathogenic YFV strains by mAbs targeting YFV E protein. Each of the antibodies isolated was tested for ability to neutralize YFV-17D in a focus reduction neutralization test (FRNT) in Vero cells. While most antibodies did not neutralize YFV-17D infection, two mAbs showed some inhibitory activity: YFV-121 was moderately neutralizing, with a half maximal inhibitory concentration of 202 ng/mL (FIG. 1B), and YFV-136 showed exceptional potency, with an $IC_{50}$ below 10 ng/mL. The inventor next tested YFV-136 for its ability to neutralize pathogenic YFV strains under BSL-3 conditions. YFV-136 also neutralized Asibi, Kouma, and a different 17D vaccine strain with high potency (FIGS. 2B-D). At lower antibody concentrations, the inventor observed modest enhancement of infectivity in this assay, possibly due to aggregation of virions, as has been seen with other anti-flavivirus antibodies in cells lacking Fcγ receptors (Haslwanter et al., 2017).

Figure 3A:
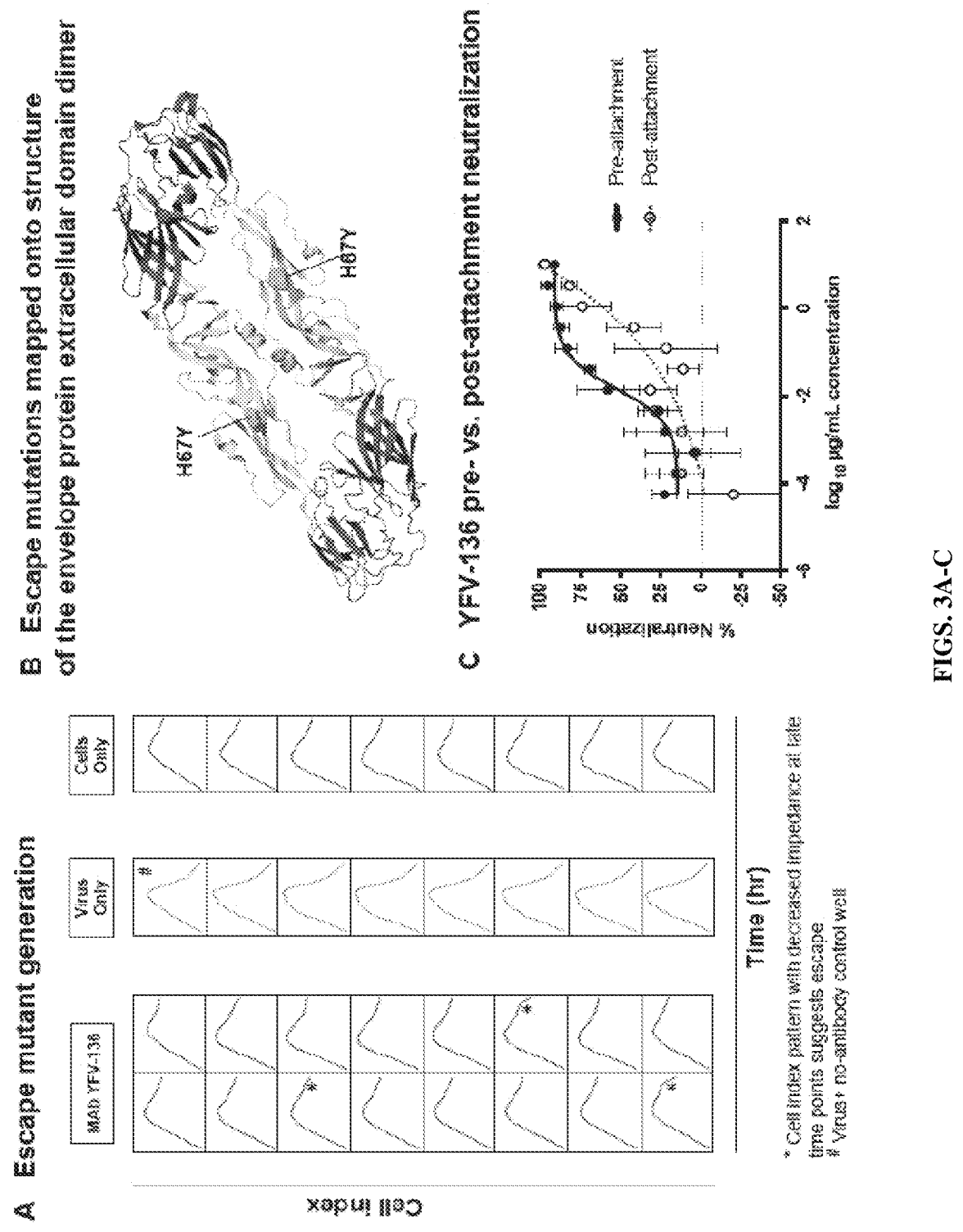

YFV-136 escape mutation studies identify a substitution at H67 that abrogates neutralization capacity. The inventor next identified the epitope of YFV-136. To identify mutations in the YFV envelope protein that allow escape from YFV-136 neutralization, he used a real-time cell analysis (RTCA) assay. This high—throughput system monitors cell impedance and thus detects cytopathic effect (CPE) over time, which allows for identification of escape viruses by observation of delayed (CPE) after incubating virus with a neutralizing concentration of antibody. For these studies, YFV-17D was incubated with 5 µg/mL of YFV-136 in 16 wells of a 96-well plate. In 13 of 16 wells, complete neutralization and maintenance of cell monolayer integrity was observed throughout the study. However, 3 of 16 wells showed a late CPE phenotype, suggesting selection of variant viruses that subvert YFV-136 neutralization (FIG. 3A). Supernatants from these wells were harvested and again incubated with 5 µg/mL of YFV-136 on the RTCA instrument to confirm escape. In this second round, CPE developed rapidly, similar to a virus-only control, confirming selection of a population of virus that is refractory to YFV-136 neutralization.

Confirmation of viral escape using RTCA was followed by outgrowth of virus in the presence of 10 µg/mL YFV-136 to provide further purifying selection. Viral RNA was then isolated, and prM and E genes amplified and sequenced. In all 3 escape viruses, a single histidine to tyrosine substitution at position 67 on DII of YFV E was identified (FIG. 3B). This residue in the b-strand is conserved across all YFV genotypes, suggesting this escape phenotype likely would be recapitulated in fully virulent YFV strains. Overall, escape mutation studies identified a key residue in DII responsible for escape from YFV-136, suggesting this mAb functions by binding an epitope including H67 on DII.

YFV-136 neutralizes YFV-17D virus at a post-attachment step. Neutralizing antibodies can target major stages in the viral replication cycle, including, but not limited to, attachment, entry, or egress. Antibodies targeting YFV and other flaviviruses typically function at one or more of these replication steps. To determine the mechanism of action for the most potently neutralizing antibody, YFV-136, the inventor performed pre- and post-attachment neutralization assays (FIG. 3C). In the pre-attachment variation, virus and antibody were pre-mixed prior to addition to Vero cell culture monolayers. In the post-attachment assay, virus was incubated first on cells to allow attachment, the excess, unbound virus was washed away, and subsequently antibody was added. YFV-136 neutralized infection in both assays, suggesting that at least part of its inhibitory activity occurs after viral attachment, albeit with some diminished potency.

YFV-136 protects hamsters from lethal YFV challenge. Because YFV-136 is the most potently neutralizing antibody in the inventor's panel, the inventor studied its activity in vivo. He first assessed the activity of YFV-136 in a model of YFV disease in Syrian golden hamsters. This model recapitulates many aspects of human YFV infections, including viscerotropism primarily affecting the liver, and has been used to assess therapeutic efficacy of small-molecules and antibody drugs (Julander et al., 2014; 2017; Tesh et al., 2001). Prior to the in vivo study, the inventor tested whether the YFV-136 neutralized the hamster-adapted YFV Jimenez strain. MAb YFV-136 exhibited a PRNT50 value of 0.5 µg/mL when tested in a PRNT assay in Vero 76 cell monolayers using the hamster-adapted YFV Jimenez strain. Next, animals were administered a 6×LD50 dose of the virulent, hamster-adapted Jimenez strain of YFV by an intraperitoneal route. At 3 days post-infection (dpi), 10 animals were treated with 50 mg/kg of YFV-136, and 15 animals with 10 mg/kg of control antibody DENV-2D22 (Table A). Whereas 12 of 15 animals in the control group succumbed to infection, all animals in the YFV-136 group survived the 21-day study (FIG. 4A). Animals treated with YFV-136 showed transient weight loss after antibody treatment, but quickly recovered and gained weight throughout the remaining course of the study (FIG. 4B). Viremia was assessed in all animals at day 6 after inoculation. While control mAb (DENV-2D22)-treated animals showed substantial viremia, animals treated with YFV-136 showed a significant reduction (FIG. 4C). Finally, the inventor assessed the ability of YFV-136 to prevent YFV-induced liver damage in hamsters by measuring serum alanine aminotransferase (ALT). Whereas animals treated with an isotype control showed markedly increased serum ALT, animals treated with YFV-136 had lower ALT levels, suggesting YFV-136 protects hamsters from hepatic damage induced by the hamster-adapted YFV stain Jimenez.

YFV-136 protects humanized mice from lethal YFV challenge. The inventor recently developed a YFV infection model in mice engrafted with human hepatocytes (hFRG mice) (Bailey et al., 2020). Immunodeficient hFRG mice have three genetic lesions (fumarylacetoacetate hydrolase [Fah]$^{-/-}$, Rag2$^{-/-}$, and Il2ry$^{-/-}$ on a C57BL/6J background), which together with specifically-timed dietary modifications, facilitate the durable replacement of murine hepatocytes with transplanted human hepatocytes (Azuma et al., 2007). YFV-infected hFRG mice developed disease that recapitulated many features of YF in humans including massive hepatic infection and injury (Bailey et al., 2020). Here, the inventor tested the therapeutic activity of YFV-136 in this highly susceptible hepatotropic model. hFRG mice were administered a single 10 mg/kg dose of YFV-136 or isotype control mAb (DENV-2D22) at 8 hr after inoculation with 2×10$^5$ focus forming units (FFU) with wt YFV-Dakar, a highly pathogenic West African strain of YFV. By 4 dpi, all isotype mAb-treated hFRG mice displayed substantial signs of disease: two were dead, the other three were moribund, and all had lost 15-25% of their initial body weight (FIGS. 5A-B). In contrast, hFRG mice that were inoculated with YFV and treated with YFV-136 mAb appeared healthy and exhibited minimal weight loss. The reduced disease observed in the YFV-136-treated group corresponded with significant (1,000-fold) reductions in YFV burden in the serum and liver (FIG. 5C-D), and normal levels of liver synthetic function (as measured by the prothrombin time [PT]), hepatocyte damage (alanine aminotransferase [ALT]), biliary function (bilirubin), and detoxification capacity (ammonium) (FIGS. 5E-H). Thus, YFV-136 therapy given 8 hr post-infection was highly protective in the susceptible hFRG mouse model of YFV infection and liver disease.

Identification of antigenic site for mAb YFV-136 using HDX-MS studies. Using HDX-MS, a technique in which antibody binding reduces deuterium labeling of surface-exposed viral protein residues, we identified peptides on the YFV-E protein that that are occluded by binding of YFV-136 Fab fragments (FIG. 6A). The start and end residues and the amino acid sequences of the representative E protein peptides that showed differential deuteration in the absence of presence of YFV-136 are shown in (FIG. 6B). The E protein domain II (DII) near the fusion loop showed the most protection following YFV-136 Fab binding. Some protection against deuteration also was observed in the dimer interface and in DIII.

Example 3—Discussion

Yellow fever virus is a re-emerging arbovirus with epidemic potential. While a highly effective live-attenuated vaccine is available for human use, safety and manufacturing concerns warrant new countermeasure development. Here, the inventor isolated a panel of naturally occurring fully human monoclonal antibodies that bind to the primary target of anti-YFV functional humoral immunity, the E glycoprotein. Two mAbs, YFV-121 and YFV-136, showed neutralization activity against YFV-17D, with YFV-136 showing exceptional potency with IC$_{50}$<10 ng/mL. The potency of YFV-136 represents one of the most potent mAbs against YFV ever isolated, prompting studying of this mAb in detail. This mAb also neutralizes several virulent strains of YFV. Both neutralizing mAbs bind to overlapping antigenic sites as determined by competition binding, suggesting recognition of a common major site of neutralization vulnerability. Antibody escape mutant virus studies identified H67 on DII as a critical residue for the function of YFV-136. The inventor shows that YFV-136 functions to inhibit infection at least in part at a post-attachment step in the viral lifecycle. Finally, this mAb was highly efficacious in two different small animal models of YFV infection even when administered after infection, suggesting YFV-136 warrants further development as a therapeutic monoclonal antibody for use in humans.

The antigenic site recognized by YFV-136, which lies proximal to the fusion loop (FL) on E protein domain II, has been previously implicated as important for humoral immunity induced by YFV-17D vaccination [30]. MAbs characterized in Wec et al. display a propensity for pairings of heavy and light chain genes encoded by antibody variable genes IGHV4-4+IGLV1-51, suggesting a public clonotype is elicited by YFV-17D vaccination. These data complement these findings, as YFV-136 also uses this pairing. It is possible that the efficacy of YFV-17D hinges on its ability to elicit antibodies to this site, since both neutralizing mAbs the inventor isolated from these donors are members of this public clonotype. However, the number of mAbs isolated here is not sufficient to make a definitive conclusion in this regard. To date, very few studies probing the humoral immune response to YFV have studied the circulating B cells of survivors of natural infection.

Escape mutation here suggest that, while YFV-136 binds to recombinant, monomeric E protein, it may have the ability to interact with both E protomers within the dimeric, membrane bound structure of YFV-E. This possibility is suggested by the fact that the single escape mutant isolated showed an amino acid substitution in DII. It is most likely that critical contacts are focused on the H67 region of DII, but that interactions with DI in the adjacent E protein suggested by the HDX-MS data are possible in the context of binding to whole YFV virions. It is possible that these interactions across adjacent E proteins is what differentiates YFV-136 from YFV-121, a less potent antibody that the inventor showed to bind to a similar/overlapping antigenic site. Alternatively, YFV-136 simply engages YFV E on the virion surface at higher affinity, although binding by ELISA suggests both YFV-121 and YFV-136 bind to recombinant E with equal strength. Higher resolution structural studies are needed to understand these interactions better and to identify a more complete binding footprint by YFV-136.

TABLE A

The effect of delayed treatment (3 dpi) with mAb YFV-136 in a 21-day Syrian golden hamster model of YFV Jimenez strain infection and disease

| MAb treatment | Dose of mAb given on 3 dpi (mg/kg) | Virus given i.p. or 0 dpi | Alive/total | Mean day of death ± SD | Mean body weight change[b] (grams ± SD) | Serum virus titer on 4 dpi ($CCID_{50}$/mL ± SD) | Serum alanine aminotransferase test on 6 dpi (mean IU/L ± SD) |
|---|---|---|---|---|---|---|---|
| YFV-136 | 50 | YFV[a] | 10/10 | >21 ± 0.0** | −5.2 ± 6.7 | 4.1 ± 2.2 | 114 ± 26* |
| Isotype control (DENV 2D22) | 10 | YFV[a] | 3/15 | 7.5 ± 1.4 | −8.9 ± 9.9 | 5.4 ± 2.3 | 214 ± 120 |
| Normal controls | — | Sham | 5/5 | >21.0 ± 0.0** | 3.0 ± 2.1** | 1.7 ± 0.0** | 80 ± 3* |

[a]Hamster-adapted YFV Jimenez strain (Julander et al., 2014).
[b]Difference between weight on 4 and 5 dpi, representing maximal weight change in this study.
**P < 0.001,
*P < 0.01, as compared to control treatment.

TABLE 1

NUCLEOTIDE SEQUENCES FOR ANTIBODY VARIABLE REGIONS

| Clone | SEQ ID NO: | Chain | Variable Sequence Region |
|---|---|---|---|
| YFV-136 | 1 | heavy | CAGGTGCAGCTGCAGGAGTCGGGCCCAGGACTGGTGAAGCCTTCGGGGACCCTGTCCCTCACCTGCGCT GTCTCTGGTGGCTCCATCAGCAGTAGTAACTGGTGGAGTTGGGTCCGCCAGCCCCCAGGGAAGGGGCTG GAGTGGATTGGGGATATCTATCACAGTGGGAGCACCAGCTACAACCCGTCCCTCAAGAGTCGAGTCACC ATATCAGTAGACAGGTCCAAGAACCAGTTCTCCCTGAAGCTGAGCTCTGTGACCGCCGCGGACACGGCC GTGTATTACTGTGCGAGAGCCCCCCTTGTTAACTGGTACTACTTTGATTACTGGGGCAGGGAACCCTG GTCACCGTCTCCTCA |
| | 2 | light | CAGTCTGTGTTGACGCAGCCGCCCTCAGTGTCTGCGGCCCCAGGACAGAAGGTCACCATCTCCTGCTCT GGAAGCAGCTCCAACATTGGGAATAATTATGTATCCTGGTACCAGCAACTCCCAGGAACAGCCCCCAAA CTCCTCATTTATGACAATAATAAGGGACCCTCAGGGATTCCTGACCGATTCTCTGGCTCCAAGTCTGGC ACGTCAGCCACCCTGGGCATCACCGGACTCCAGACTGGGGACGAGGCCGATTATTACTGCGGAACATGG GATACCAGCCTGAGTGCTGGCCGGGTGTTCGGCGGAGGGACCAAGCTGACCGTCCTA |
| YFV-121 | 3 | heavy | GAGGTGCAGCTGGTGGAGTCTGGGGGAGGCTTGGTTCAGCCTGGGGGGTCCCTGAGACTCTCCTGTGCA GCCTCTGGATTCACCTTCAGTAGCTATAGCATGAACTGGGTCCGCCAGGCTCCAGGGAAGGGGCTGGAG TGGGTTTCATACATTAGTAGTAGTAGTAGAACCATATACTACGCAGACTCTGTGAAGGGCCGATTCACC ATCTCCAGAGACAATGCCAAGAACTCACTGGATCTGCAAATGAACAGCCTGAGAGACGAGGACACGGCT GTGTATTACTGTGCGAGAGAGGTTAGCAGCCATGGTTATAGGTACTGGGGCCAGGGAACCCTGGTCACC GTCTCCTCA |
| | 4 | light | GAAATTGTGTTGACACAGTCTCCAGCCACCCTGTCTTTGTCTCCAGGGGAAAGAGCCACCCTCTCCTGC AGGGCCAGTCAGAGTGTTAGCAGCTTCTTAGCCTGGTACCAACAGAAACCTGGCCAGGCTCCCAGGCTC CTCATCTATGATGCATCCAACAGGGCCACTGGCATCCCAGCCAGGTTCACTGGCAGTGGGTCTGGGACA GACTTCACTCTCACCATCAGCAGCCTAGAGCCTGAAGATTTTGCAGTTTATTACTGTCAGCAGCGTAGC AACTGGCCTCCGTGGACGTTCGGCCAAGGGACCAAGGTGGAAATCAAA |

TABLE 2

PROTEIN SEQUENCES FOR ANTIBODY VARIABLE REGIONS

| Clone | SEQ ID NO: | Chain | Variable Sequence Region |
|---|---|---|---|
| YFV-136 | 5 | heavy | QVQLQESGPGLVKPSGTLSLTCAVSGGSISSSNWWSWVRQPPG KGLEWIGDIYHSGSTSYNPSLKSRVTISVDRSKNQFSLKLSSV TAADTAVYYCARAPLVNWYYFDYWGQGTLVTVSS |
| | 6 | light | QSVLTQPPSVSAAPGQKVTISCSGSSSNIGNNYVSWYQQLPGT APKLLIYDNNKGPSGIPDRFSGSKSGTSATLGITGLQTGDEAD YYCGTWDTSLSAGRVFGGGTKLTVL |
| YFV-121 | 7 | heavy | EVQLVESGGGLVQPGGSLRLSCAASGFTFSSYSMNWVRQAPGK GLEWVSYISSSSRTIYYADSVKGRFTISRDNAKNSLDLQMNSL RDEDTAVYYCAREVSSHGYRYWGQGTLVTVSS |
| | 8 | light | EIVLTQSPATLSLSPGERATLSCRASQSVSSFLAWYQQKPGQA PRLLIYDASNRATGIPARFTGSGSGTDFTLTISSLEPEDFAVY YCQQRSNWPPWTFGQGTKVEIK |

TABLE 3

CDR HEAVY CHAIN SEQUENCES

| Clone | CDRH1 | CDRH2 | CDRH3 |
|---|---|---|---|
| YFV-136 | GGSISSSNW (SEQ ID NO: 9) | IYHSGST (SEQ ID NO: 10) | ARAPLVNWYYFDY (SEQ ID NO: 11) |
| YFV-121 | GFTFSSYS (SEQ ID NO: 12) | ISSSSRTI (SEQ ID NO: 13) | AREVSSHGYRY (SEQ ID NO: 14) |

TABLE 4

CDR LIGHT CHAIN SEQUENCES

| Clone | CDRL1 | CDRL2 | CDRL3 |
|---|---|---|---|
| YFV-136 | SSNIGNNY (SEQ ID NO: 15) | DNN | GTWDTSLSAGRV (SEQ ID NO: 16) |
| YFV-121 | QSVSSF (SEQ ID NO: 17) | DAS | QQRSNWPPWT (SEQ ID NO: 18) |

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. References

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567
U.S. Pat. No. 4,867,973
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,565,332
U.S. Pat. No. 5,856,456
U.S. Pat. No. 5,880,270
U.S. Pat. No. 6,485,982
"Antibodies: A Laboratory Manual," Cold Spring Harbor Press, Cold Spring Harbor, N.Y., 1988.
Abbondanzo et al., *Am. J. Pediatr. Hematol. Oncol.* 12(4): 480-489, 1990.
Allred et al., *Arch. Surg.* 125(1), 107-113: 1990.
Atherton et al., *Biol. of Reproduction* 32: 155-171, 1985.
Barzon et al., *Euro Surveill.* 11: 21(32), 2016.
Beltramello et al., *Cell Host Microbe* 8: 271-283, 2010.
Brown et al., *J. Immunol. Meth.* 130(1): 111-121, 1990.
Campbell, In: *Monoclonal Antibody Technology, Laboratory Techniques in Biochemistry and Molecular Biology*, Vol. 13, Burden and Von Knippenberg, Eds. pp. 75-83, Amsterdam, Elsevier, 1984.
Capaldi et al., *Biochem. Biophys. Res. Comm.* 74(2):425-433, 1977.
De Jager et al., *Semin. Nucl. Med.* 23(2): 165-179, 1993.
Dholakia et al., *J. Biol. Chem.* 264: 20638-20642, 1989.
Diamond et al., *J. Virol.* 77: 2578-2586, 2003.
Doolittle and Ben-Zeev, *Methods Mol. Biol.* 109: 215-237, 1999.
Duffy et al., *N. Engl. J. Med.* 360: 2536-2543, 2009.
Elder et al. Infections, infertility and assisted reproduction. Part II: Infections in reproductive medicine & Part III: Infections and the assisted reproductive laboratory. Cambridge UK: Cambridge University Press; 2005.
Gefter et al., *Somatic Cell Genet.* 3: 231-236, 1977.
Gornet et al., *Semin Reprod Med.* 34(5): 285-292, 2016.
Gulbis and Galand, *Hum. Pathol.* 24(12): 1271-1285, 1993.

Halfon et al., *PLoS ONE* 5(5): e10569, 2010
Hessell et al., *Nature* 449: 101-104, 2007.
Khatoon et al., *Ann. of Neurology* 26: 210-219, 1989.
King et al., *J. Biol. Chem.* 269: 10210-10218, 1989.
Kohler and Milstein, *Eur. J. Immunol.* 6: 511-519, 1976.
Kohler and Milstein, *Nature* 256: 495-497, 1975.
Kyte and Doolittle, *J. Mol. Biol.* 157(1): 105-132, 1982.
Lo et al., *J. Biol. Chem.* 3; 292(9):3900-3908, 2017.
Mansuy et al., *Lancet Infect Dis.* 16(10): 1106-7, 2016.
Nakamura et al., In: *Enzyme Immunoassays: Heterogeneous and Homogeneous Systems*, Chapter 27, 1987.
O'Shannessy et al., *J. Immun. Meth.* 99: 153-161, 1987.
Persic et al., *Gene* 187: 1, 1997
Potter and Haley, *Meth. Enzymol.* 91: 613-633, 1983.
Purpura et al., *Lancet Infect Dis.* 16(10): 1107-8, 2016.
Remington's Pharmaceutical Sciences, 15th Ed., 3: 624-652, 1990.
Tang et al., *J. Biol. Chem.* 271: 28324-28330, 1996.
Wawrzynczak & Thorpe, In: *Immunoconjugates, Antibody Conjugates In Radioimaging And Therapy of Cancer*, Vogel (Ed.), NY, Oxford University Press, 28, 1987.
Yu et al., *J Immunol Methods* 336: 142-151, 2008.
Bauer, J. H. and N. P. Hudson, *J Exp Med*, 48(1): p. 147-53, 1928.
Gaythorpe, K. A., et al., *Elife*, 10. 2021.
Monath, T. P. and P. F. Vasconcelos, *J Clin Virol*, 64: p. 160-73, 2015.
Douam, F. and A. Ploss, *Trends Microbiol*, 26(11): p. 913-928, 2018.
Cunha, M. S., et al., *Sci Rep*, 10(1): p. 15751, 2020.
Chambers, T. J., et al., *Annu Rev Microbiol*, 44: p. 649-88, 1990.
Daffis, S., et al., *Virology*, 337(2): p. 262-72, 2005.
Pierson, T. C. and M. Kielian, *Curr Opin* Virol, 3(1): p. 3-12, 2013.
Ryman, K. D., et al., *J Gen Virol*, 78 (Pt 6): p. 1353-6, 1997.
Brandriss, M. W., et al., *J Gen Virol*, 67 (Pt 2): p. 229-34, 1986.
Cammack, N. and E. A. Gould, *Virology*, 150(2): p. 333-41, 1986.
Schlesinger, J. J., et al., *Virology*, 125(1): p. 8-17, 1983.
Schlesinger, J. J., et al., *J Immunol*, 135(4): p. 2805-9, 1985.
Schlesinger, J. J. et al., *Virology*, 192(1): p. 132-41, 1993.
Putnak, J. R. and J. J. Schlesinger, *J Gen Virol*, 71 (Pt 8): p. 1697-702, 1990.
Smith, S. A., et al., *J Virol*, 90(2): p. 780-9, 2016.
Dejnirattisai, W., et al., *Science*, 328(5979): p. 745-8, 2010.
Rodenhuis-Zybert, I. A., et al., *PLoS Pathog*, 6(1): p. e1000718, 2010.
Shearer, F. M., et al., *Lancet Infect Dis*, 17(11): p. 1209-1217, 2017.
Casey, R. M., et al., *N Engl J Med*, 381(5): p. 444-454, 2019.
Wilder-Smith, A., et al., *Ann Intern Med*, 171(2): p. 145-146, 2019.
Lu, X., et al., *Cell Rep*, 26(2): p. 438-446 e5, 2019.
Julander, J. G., et al., *Antiviral Res*, 103: p. 32-8, 2014.
Thibodeaux, B. A., et al., *Antiviral Res*, 94(1): p. 1-8, 2012.
Haslwanter, D., et al., *A PLoS Pathog*, 13(9): p. e1006643, 2017.
Tesh, R. B., et al., *J Infect Dis*, 183(10): p. 1431-6, 2001.
Julander, J. G., et al., *Antiviral Res*, 137: p. 14-22, 2017.
Bailey, A. L., et al., *Proc Natl Acad Sci USA*, 117(51): p. 32648-32656, 2020.
Azuma, H., et al., *Nat Biotechnol*, 25(8): p. 903-10, 2007.
Wec, A. Z., et al., *Proc Natl Acad Sci USA*, 117(12): p. 6675-6685, 2020.
Smith, S. A. and J. E. Crowe, Jr., *Microbiol Spectr*, 3(1): p. AID-0027-2014, 2015.
Williamson, L. E., et al., *Cell*, 183(7): p. 1884-1900 e23, 2020.
Breit, T. M., et al., *Blood*, 82(10): p. 3063-74, 1993.

---

What is claimed is:

1. A method of detecting a Yellow Fever Virus (YFV) infection in a subject comprising:
   (a) contacting a sample from said subject with an antibody or antibody fragment comprising heavy chain CDR1-3 sequences comprising SEQ ID NO: 15, DNN and SEQ ID NO: 16 and light chain CDR1-3 sequences comprising SEQ ID NO: 17, DAS and SEQ ID NO: 18; and
   (b) detecting YFV in said sample by binding of said antibody or antibody fragment to a YFV antigen in said sample.

2. A method of treating a subject infected with Yellow Fever Virus (YFV), or reducing the likelihood of infection of a subject at risk of contracting YFV, comprising delivering to said subject an antibody or antibody fragment comprising heavy chain CDR1-3 sequences comprising SEQ ID NO: 15, DNN and SEQ ID NO: 16 and light chain CDR1-3 sequences comprising SEQ ID NO: 17, DAS and SEQ ID NO: 18.

3. The method of claim 2, the antibody or antibody fragment is encoded by light and heavy chain variable sequences comprising SEQ ID NOS: 2 and 1 or 4 and 3, respectively.

4. The method of claim 2, the antibody or antibody fragment is encoded by light and heavy chain variable sequences having 95% identity to SEQ ID NOS: 2 and 1 or 4 and 3, respectively.

5. The method of claim 2, wherein said antibody or antibody fragment is encoded by light and heavy chain variable sequences having 70%, 80%, or 90% identity to SEQ ID NOS: 2 and 1 or 4 and 3, respectively.

6. The method of claim 2, wherein said antibody or antibody fragment comprises light and heavy chain variable sequences comprising SEQ ID NOS: 6 and 5 or 8 and 7, respectively.

7. The method of claim 2, wherein said antibody or antibody fragment comprises light and heavy chain variable sequences having 70%, 80% or 90% identity to SEQ ID NOS: 6 and 5 or 8 and 7, respectively.

8. The method of claim 2, wherein said antibody or antibody fragment comprises light and heavy chain variable sequences having 95% identity to SEQ ID NOS: 6 and 5 or 8 and 7, respectively.

9. The method of claim 2, wherein the antibody fragment is a recombinant scFv (single chain fragment variable) antibody, Fab fragment, F(ab')2 fragment, or Fv fragment.

10. The method of claim 2, wherein said antibody is an IgG, or a recombinant IgG antibody or antibody fragment comprising an Fc portion mutated to eliminate or enhance FcR interactions, to increase half-life and/or increase therapeutic efficacy, or glycan modified to eliminate or enhance FcR interactions.

11. The method of claim 2, wherein said antibody is a chimeric antibody or a bispecific antibody.

12. The method of claim 2, wherein said antibody or antibody fragment is administered prior to infection or after infection.

13. The method of claim 2, wherein said subject is a pregnant female, a sexually active female, or a female undergoing fertility treatments.

14. The method of claim 2, wherein delivering comprises antibody or antibody fragment administration, or genetic delivery with an RNA or DNA sequence or vector encoding the antibody or antibody fragment.

15. A monoclonal antibody, wherein the antibody or antibody fragment comprises heavy chain CDR1-3 sequences comprising SEQ ID NO: 15, DNN and SEQ ID NO: 16 and light chain CDR1-3 sequences comprising SEQ ID NO: 17, DAS and SEQ ID NO: 18.

16. A hybridoma or engineered cell encoding an antibody or antibody fragment wherein the antibody or antibody fragment is comprises heavy chain CDR1-3 sequences comprising SEQ ID NO: 15, DNN and SEQ ID NO: 16 and light chain CDR1-3 sequences comprising SEQ ID NO: 17, DAS and SEQ ID NO: 18.

17. A vaccine formulation comprising one or more antibodies or antibody fragments comprising heavy chain CDR1-3 sequences comprising SEQ ID NO: 15, DNN and SEQ ID NO: 16 and light chain CDR1-3 sequences comprising SEQ ID NO: 17, DAS and SEQ ID NO: 18.

18. The method of claim 2, wherein the subject is a pregnant female.

19. The method of claim 1, wherein said antibody or antibody fragment comprises light and heavy chain variable sequences comprising SEQ ID NOS: 6 and 5 or 8 and 7, respectively.

20. The method of claim 1, wherein said antibody or antibody fragment comprises light and heavy chain variable sequences having 70%, 80%, 90% or 95% identity to SEQ ID NOS: 6 and 5 or 8 and 7, respectively.

21. The hybridoma or engineered cell of claim 16, wherein said antibody or antibody fragment comprises light and heavy chain variable sequences comprising SEQ ID NOS: 6 and 5 or 8 and 7, respectively.

22. The hybridoma or engineered cell of claim 16, wherein said antibody or antibody fragment comprises light and heavy chain variable sequences having 70%, 80%, 90% or 95% identity to SEQ ID NOS: 6 and 5 or 8 and 7, respectively.

23. The antibody or antibody fragment of claim 15, wherein said antibody or antibody fragment comprises light and heavy chain variable sequences comprising SEQ ID NOS: 6 and 5 or 8 and 7, respectively.

24. The antibody or antibody fragment of claim 15, wherein said antibody or antibody fragment comprises light and heavy chain variable sequences having 70%, 80%, 90% or 95% identity to SEQ ID NOS: 6 and 5 or 8 and 7, respectively.

25. The monoclonal antibody or antibody fragment of claim 15, wherein said antibody a recombinant IgG antibody or antibody fragment comprising an Fc portion mutated to eliminate or enhance FcR interactions, to increase half-life and/or increase therapeutic efficacy, or glycan modified to eliminate or enhance FcR interactions.

26. The monoclonal antibody or antibody fragment of claim 25, wherein the antibody or antibody fragment comprises a a LALA, LALA-PG, N297, GASD/ALIE, DHS, YTE or LS mutation, or wherein glycans are added to or removed from the or antibody fragment, or the antibody or antibody fragment is expressed in a cell line engineered that produces a defined non-natural glycosylating pattern on the antibody or antibody fragment.

27. The monoclonal antibody or antibody fragment of claim 10, wherein the antibody or antibody fragment comprises a a LALA, LALA-PG, N297, GASD/ALIE, DHS, YTE or LS mutation, or wherein glycans are added to or removed from the or antibody fragment, or the antibody or antibody fragment is expressed in a cell line engineered that produces a defined non-natural glycosylating pattern on the antibody or antibody fragment.

* * * * *

SEQUENCE LISTING

```
Sequence total quantity: 21
SEQ ID NO: 1            moltype = DNA  length = 360
FEATURE                 Location/Qualifiers
misc_feature            1..360
                        note = Synthetic polynucleotide
source                  1..360
                        mol_type = other DNA
                        organism = synthetic construct
SEQUENCE: 1
caggtgcagc tgcaggagtc gggcccagga ctggtgaagc cttcggggac cctgtccctc   60
acctgcgctg tctctggtgg ctccatcagc agtagtaact ggtggagttg ggtccgcag   120
cccccaggga aggggctgga gtggattggg gatatctatc acagtgggag caccagctac  180
aacccgtccc tcaagagtcg agtcaccata tcagtagaca ggtccaagaa ccagttctcc   240
ctgaagctga gctctgtgac cgccgcggac acggccgtgt attactgtgc gagagccccc   300
cttgttaact ggtactactt tgattactgg ggccaggaa ccctggtcac cgtctcctca    360

SEQ ID NO: 2            moltype = DNA  length = 333
FEATURE                 Location/Qualifiers
misc_feature            1..333
                        note = Synthetic polynucleotide
source                  1..333
                        mol_type = other DNA
                        organism = synthetic construct
SEQUENCE: 2
cagtctgtgt tgacgcagcc gccctcagtg tctgcggccc caggacagaa ggtcaccatc   60
tcctgctctg gaagcagctc caacattggg aataattatg tatcctggta ccagcaactc  120
ccaggaacag cccccaaact cctcatttat gacaataata agggaccctc agggattcct  180
gaccgattct ctggctccaa gtctggcacg tcagccaccc tgggcatcac cggactccag  240
actgggacg aggccgatta ttactgcgga acatgggata ccagcctgag tgctggccgg  300
gtgttcggcg gagggaccaa gctgaccgtc cta                              333

SEQ ID NO: 3            moltype = DNA  length = 354
FEATURE                 Location/Qualifiers
```

```
misc_feature            1..354
                        note = Synthetic polynucleotide
source                  1..354
                        mol_type = other DNA
                        organism = synthetic construct
SEQUENCE: 3
gaggtgcagc tggtggagtc tgggggaggc ttggttcagc ctgggggtc cctgagactc      60
tcctgtgcag cctctggatt caccttcagt agctatagca tgaactgggt ccgccaggct    120
ccagggaagg ggctggagtg ggtttcatac attagtagta gtagtagaac catatactac    180
gcagactctg tgaagggccg attcaccatc tccagagaca atgccaagaa ctcactggat    240
ctgcaaatga acagcctgag agacgaggac acggctgtgt attactgtgc gagagaggtt    300
agcagccatg gttataggta ctggggccag ggaaccctgg tcaccgtctc ctca          354

SEQ ID NO: 4             moltype = DNA  length = 324
FEATURE                  Location/Qualifiers
misc_feature             1..324
                         note = Synthetic polynucleotide
source                   1..324
                         mol_type = other DNA
                         organism = synthetic construct
SEQUENCE: 4
gaaattgtgt tgacacagtc tccagccacc ctgtctttgt ctccagggga aagagccacc     60
ctctcctgca gggccagtca gagtgttagc agcttcttag cctggtacca acagaaacct    120
ggccaggctc ccaggctcct catctatgat gcatccaaca gggccactgg catcccagcc    180
aggttcactg gcagtgggtc tgggacagac ttcactctca ccatcagcag cctagagcct    240
gaagattttg cagtttatta ctgtcagcag cgtagcaact ggcctccgtg gacgttcggc    300
caagggacca aggtggaaat caaa                                           324

SEQ ID NO: 5             moltype = AA  length = 120
FEATURE                  Location/Qualifiers
REGION                   1..120
                         note = Synthetic polypeptide
source                   1..120
                         mol_type = protein
                         organism = synthetic construct
SEQUENCE: 5
QVQLQESGPG LVKPSGTLSL TCAVSGGSIS SSNWWSWVRQ PPGKGLEWIG DIYHSGSTSY     60
NPSLKSRVTI SVDRSKNQFS LKLSSVTAAD TAVYYCARAP LVNWYYFDYW GQGTLVTVSS    120

SEQ ID NO: 6             moltype = AA  length = 111
FEATURE                  Location/Qualifiers
REGION                   1..111
                         note = Synthetic polypeptide
source                   1..111
                         mol_type = protein
                         organism = synthetic construct
SEQUENCE: 6
QSVLTQPPSV SAAPGQKVTI SCSGSSSNIG NNYVSWYQQL PGTAPKLLIY DNNKGPSGIP     60
DRFSGSKSGT SATLGITGLQ TGDEADYYCG TWDTSLSAGR VFGGGTKLTV L              111

SEQ ID NO: 7             moltype = AA  length = 118
FEATURE                  Location/Qualifiers
REGION                   1..118
                         note = Synthetic polypeptide
source                   1..118
                         mol_type = protein
                         organism = synthetic construct
SEQUENCE: 7
EVQLVESGGG LVQPGGSLRL SCAASGFTFS SYSMNWVRQA PGKGLEWVSY ISSSSRTIYY     60
ADSVKGRFTI SRDNAKNSLD LQMNSLRDED TAVYYCAREV SSHGYRYWGQ GTLVTVSS      118

SEQ ID NO: 8             moltype = AA  length = 108
FEATURE                  Location/Qualifiers
REGION                   1..108
                         note = Synthetic polypeptide
source                   1..108
                         mol_type = protein
                         organism = synthetic construct
SEQUENCE: 8
EIVLTQSPAT LSLSPGERAT LSCRASQSVS SFLAWYQQKP GQAPRLLIYD ASNRATGIPA     60
RFTGSGSGTD FTLTISSLEP EDFAVYYCQQ RSNWPPWTFG QGTKVEIK                 108

SEQ ID NO: 9             moltype = AA  length = 9
FEATURE                  Location/Qualifiers
REGION                   1..9
                         note = Synthetic polypeptide
source                   1..9
                         mol_type = protein
                         organism = synthetic construct
```

```
SEQUENCE: 9
GGSISSSNW                                                                        9

SEQ ID NO: 10           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 10
IYHSGST                                                                          7

SEQ ID NO: 11           moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 11
ARAPLVNWYY FDY                                                                  13

SEQ ID NO: 12           moltype = AA  length = 8
FEATURE                 Location/Qualifiers
REGION                  1..8
                        note = Synthetic polypeptide
source                  1..8
                        mol_type = protein
                        organism = synthetic construct
SEQUENCE: 12
GFTFSSYS                                                                         8

SEQ ID NO: 13           moltype = AA  length = 8
FEATURE                 Location/Qualifiers
REGION                  1..8
                        note = Synthetic polypeptide
source                  1..8
                        mol_type = protein
                        organism = synthetic construct
SEQUENCE: 13
ISSSSRTI                                                                         8

SEQ ID NO: 14           moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 14
AREVSSHGYR Y                                                                    11

SEQ ID NO: 15           moltype = AA  length = 8
FEATURE                 Location/Qualifiers
REGION                  1..8
                        note = Synthetic polypeptide
source                  1..8
                        mol_type = protein
                        organism = synthetic construct
SEQUENCE: 15
SSNIGNNY                                                                         8

SEQ ID NO: 16           moltype = AA  length = 12
FEATURE                 Location/Qualifiers
REGION                  1..12
                        note = Synthetic polypeptide
source                  1..12
                        mol_type = protein
                        organism = synthetic construct
SEQUENCE: 16
GTWDTSLSAG RV                                                                   12

SEQ ID NO: 17           moltype = AA  length = 6
FEATURE                 Location/Qualifiers
REGION                  1..6
                        note = Synthetic polypeptide
source                  1..6
                        mol_type = protein
```

-continued

```
SEQUENCE: 17
QSVSSF                                                              6

SEQ ID NO: 18         moltype = AA   length = 10
FEATURE               Location/Qualifiers
REGION                1..10
                      note = Synthetic polypeptide
source                1..10
                      mol_type = protein
                      organism = synthetic construct
SEQUENCE: 18
QQRSNWPPWT                                                         10

SEQ ID NO: 19         moltype = DNA  length = 20
FEATURE               Location/Qualifiers
misc_feature          1..20
                      note = Synthetic polynucleotide
source                1..20
                      mol_type = other DNA
                      organism = synthetic construct
SEQUENCE: 19
aggtgcattg gtctgcaaat                                              20

SEQ ID NO: 20         moltype = DNA  length = 20
FEATURE               Location/Qualifiers
misc_feature          1..20
                      note = Synthetic polynucleotide
misc_feature          19
                      note = n is inosine
source                1..20
                      mol_type = other DNA
                      organism = synthetic construct
SEQUENCE: 20
tctctgctaa tcgctcaang                                              20

SEQ ID NO: 21         moltype = DNA  length = 26
FEATURE               Location/Qualifiers
misc_feature          1..26
                      note = Synthetic polynucleotide
source                1..26
                      mol_type = other DNA
                      organism = synthetic construct
SEQUENCE: 21
gttgctaggc aataaacaca tttgga                                       26
```